United States Patent
Wang et al.

(10) Patent No.: US 8,666,209 B2
(45) Date of Patent: Mar. 4, 2014

(54) DELIVERING LIGHT VIA OPTICAL WAVEGUIDE AND MULTI-VIEW OPTICAL PROBE HEAD

(75) Inventors: Feiling Wang, Medford, MA (US); Andrey Vertikov, Westwood, MA (US)

(73) Assignee: Tomophase Corporation, Burlington, MA (US)

( * ) Notice: Subject to any disclaimer, the term of this patent is extended or adjusted under 35 U.S.C. 154(b) by 0 days.

(21) Appl. No.: 13/276,281

(22) Filed: Oct. 18, 2011

(65) Prior Publication Data

US 2012/0033911 A1 Feb. 9, 2012

Related U.S. Application Data

(60) Continuation of application No. 12/767,729, filed on Apr. 26, 2010, now Pat. No. 8,041,162, which is a division of application No. 12/075,129, filed on Mar. 7, 2008, now Pat. No. 7,706,646.

(60) Provisional application No. 60/913,768, filed on Apr. 24, 2007.

(51) Int. Cl.
G02B 6/00 (2006.01)
G02B 6/06 (2006.01)
G02B 6/26 (2006.01)
G02B 6/32 (2006.01)
G02B 6/42 (2006.01)
G02B 6/44 (2006.01)

(52) U.S. Cl.
USPC ........... 385/33; 385/11; 385/31; 385/100; 362/572; 362/574

(58) Field of Classification Search
USPC ......... 385/11, 31, 33, 100, 109; 362/572, 574
See application file for complete search history.

(56) References Cited

U.S. PATENT DOCUMENTS

| | | |
|---|---|---|
| 4,402,311 A | 9/1983 | Hattori |
| 4,848,867 A | 7/1989 | Kajioka et al. |
| 4,878,492 A | 11/1989 | Sinofsky et al. |
| 4,991,938 A | 2/1991 | Buhrer et al. |
| 5,088,493 A | 2/1992 | Giannini et al. |
| 5,202,745 A | 4/1993 | Sorin et al. |
| 5,321,501 A | 6/1994 | Swanson et al. |
| 5,459,570 A | 10/1995 | Swanson et al. |

(Continued)

FOREIGN PATENT DOCUMENTS

| | | |
|---|---|---|
| CN | 2524241 | 12/2002 |
| EP | 0 429 297 | 5/1991 |

(Continued)

OTHER PUBLICATIONS

An, L., et al., "In vivo volumetric imaging of vascular perfusion within human retina and choroids with optical micro-angiography," Optics Express, 16(15):11438-11452, Jul. 2008.

(Continued)

Primary Examiner — Ryan Lepisto
Assistant Examiner — Jerry Blevins
(74) Attorney, Agent, or Firm — Perkins Coie LLP

(57) ABSTRACT

Techniques, apparatus and systems that use an optical probe head to deliver light to a target and to collect light from the target for imaging, monitoring, medical diagnostics and medical treatment applications.

6 Claims, 15 Drawing Sheets

(56) References Cited

U.S. PATENT DOCUMENTS

| | | |
|---|---|---|
| 5,659,392 A | 8/1997 | Marcus et al. |
| 5,710,630 A | 1/1998 | Essenpreis et al. |
| 5,784,162 A | 7/1998 | Cabib et al. |
| 5,803,909 A | 9/1998 | Maki et al. |
| 5,912,762 A | 6/1999 | Li et al. |
| 6,034,774 A | 3/2000 | Marcus et al. |
| 6,134,003 A | 10/2000 | Tearney et al. |
| 6,201,989 B1 | 3/2001 | Whitehead et al. |
| 6,219,565 B1 | 4/2001 | Cupp et al. |
| 6,246,818 B1 | 6/2001 | Fukushima |
| 6,252,666 B1 | 6/2001 | Mandella et al. |
| 6,282,011 B1 | 8/2001 | Tearney et al. |
| 6,377,840 B1 | 4/2002 | Gritsenko et al. |
| 6,421,164 B2 | 7/2002 | Tearney et al. |
| 6,451,009 B1 | 9/2002 | Dasilva et al. |
| 6,485,413 B1 | 11/2002 | Boppart et al. |
| 6,498,942 B1 | 12/2002 | Esenaliev et al. |
| 6,501,551 B1 | 12/2002 | Tearney et al. |
| 6,522,407 B2 | 2/2003 | Everett et al. |
| 6,549,801 B1 | 4/2003 | Chen et al. |
| 6,585,639 B1 | 7/2003 | Kotmel et al. |
| 6,608,717 B1 | 8/2003 | Medford et al. |
| 6,609,425 B2 | 8/2003 | Ogawa |
| 6,615,072 B1 | 9/2003 | Izatt et al. |
| 6,687,010 B1 | 2/2004 | Horii et al. |
| 6,709,402 B2 | 3/2004 | Dekker |
| 6,725,073 B1 | 4/2004 | Motamedi et al. |
| 6,738,144 B1 | 5/2004 | Dogariu |
| 6,753,966 B2 | 6/2004 | Von Rosenberg |
| 6,847,453 B2 | 1/2005 | Bush |
| 6,891,984 B2 | 5/2005 | Petersen et al. |
| 6,901,284 B1 | 5/2005 | Maki et al. |
| 6,903,820 B2 | 6/2005 | Wang |
| 6,903,854 B2 | 6/2005 | Gelikonov et al. |
| 6,943,881 B2 | 9/2005 | Wang |
| 7,023,563 B2 | 4/2006 | Li |
| 7,039,454 B1 | 5/2006 | Kaga et al. |
| 7,058,155 B2 | 6/2006 | Piacsek et al. |
| 7,170,574 B2 | 1/2007 | Tan et al. |
| 7,207,984 B2 | 4/2007 | Farr et al. |
| 7,254,429 B2 | 8/2007 | Schurman et al. |
| 7,259,851 B2 | 8/2007 | Wang |
| 7,263,394 B2 | 8/2007 | Wang |
| 7,428,053 B2 | 9/2008 | Feldchtein et al. |
| 7,456,965 B2 | 11/2008 | Wang |
| 7,595,879 B2 | 9/2009 | Wang |
| 7,831,298 B1 | 11/2010 | Wang et al. |
| 7,970,458 B2 | 6/2011 | Norris et al. |
| 7,999,938 B2 | 8/2011 | Wang |
| 2002/0049370 A1 | 4/2002 | Laufer et al. |
| 2002/0126347 A1 | 9/2002 | Hogan |
| 2002/0131049 A1 | 9/2002 | Schmitt |
| 2003/0020920 A1 | 1/2003 | Dave et al. |
| 2003/0114878 A1 | 6/2003 | Diederich et al. |
| 2003/0137669 A1 | 7/2003 | Rollins et al. |
| 2003/0187319 A1 | 10/2003 | Kaneko et al. |
| 2004/0001716 A1 | 1/2004 | Daou et al. |
| 2004/0140425 A1 | 7/2004 | Iizuka et al. |
| 2004/0218845 A1* | 11/2004 | Li et al. ............ 385/11 |
| 2004/0246490 A1 | 12/2004 | Wang |
| 2004/0247268 A1 | 12/2004 | Ishihara et al. |
| 2004/0258377 A1 | 12/2004 | Berkey et al. |
| 2004/0260158 A1 | 12/2004 | Hogan |
| 2005/0018202 A1 | 1/2005 | Wang |
| 2005/0053109 A1 | 3/2005 | Hogan |
| 2005/0075547 A1 | 4/2005 | Wang |
| 2005/0264904 A1* | 12/2005 | Sato et al. ............ 359/885 |
| 2005/0286055 A1 | 12/2005 | Wang |
| 2006/0079762 A1 | 4/2006 | Norris et al. |
| 2006/0089548 A1 | 4/2006 | Hogan |
| 2006/0100490 A1 | 5/2006 | Wang et al. |
| 2007/0103683 A1 | 5/2007 | Wang |
| 2007/0115476 A1 | 5/2007 | Feldchtein et al. |
| 2007/0139618 A1* | 6/2007 | DeCusatis et al. ............ 353/7 |
| 2008/0030740 A1 | 2/2008 | Wang |
| 2008/0033300 A1 | 2/2008 | Hoang et al. |
| 2008/0119701 A1 | 5/2008 | Milner et al. |
| 2009/0073444 A1 | 3/2009 | Wang |
| 2010/0014093 A1 | 1/2010 | Wang |
| 2010/0091282 A1 | 4/2010 | Wang |
| 2011/0029049 A1 | 2/2011 | Vertikov et al. |
| 2011/0063616 A1 | 3/2011 | Wang |
| 2011/0066035 A1 | 3/2011 | Norris et al. |
| 2011/0285996 A1 | 11/2011 | Wang |

FOREIGN PATENT DOCUMENTS

| | | |
|---|---|---|
| EP | 0 527 050 | 2/1993 |
| JP | 2001-066245 | 3/2001 |
| JP | 2002-013907 | 1/2002 |
| JP | 2004-317437 | 11/2004 |
| WO | 03/062802 | 7/2003 |
| WO | 2005/001522 | 1/2005 |
| WO | 2006/041997 | 4/2006 |
| WO | 2006/045013 | 4/2006 |
| WO | 2009/108950 | 9/2009 |

OTHER PUBLICATIONS

Mariampillai, A., et al., "Doppler optical cardiogram gated 2D color flow imaging at 1000 fps and 4D in vivo visualization of embryonic heart at 45 fps on a swept source OCT system," Optics Express, 15(4):1627-1638, Feb. 2007.

Yang, V., et al., "High speed, wide velocity dynamic range Doppler optical coherence tomography (Part I): System design, signal processing, and performance," Optics Express, 11(7):794-809, Apr. 2003.

European Search Report dated Nov. 18, 2010 for European Patent Application No. 05813935.3, filed Oct. 20, 2005 (9 pages).

European Search Report dated Nov. 2, 2010 for European Patent Application No. 04754292.3, filed Jun. 4, 2004 (4 pages).

Handbook of Optics, 2nd Edition, vol. 1: Fundamentals, Techniques, & Design, Optical Society of America, McGraw-Hill Professional, pp. 42.68-42.73, Sep. 1994.

International Preliminary Report on Patentability dated Dec. 22, 2005 for International Application No. PCT/US04/17649, filed Jun. 4, 2004 (7 pages).

International Preliminary Report on Patentability dated Feb. 24, 2009 for International Application No. PCT/US05/35951, filed Oct. 5, 2005 (9 pages).

International Preliminary Report on Patentability dated Nov. 5, 2009 for International Application No. PCT/US2008/061451, filed Apr. 24, 2008 (6 pages).

International Search Report and Written Opinion dated Aug. 29, 2008 for International Application No. PCT/US05/35951, filed Oct. 5, 2005 (10 pages).

International Search Report and Written Opinion dated Nov. 20, 2009 for International Application No. PCT/US2009/035773, filed Mar. 2, 2009 (7 pages).

International Search Report and Written Opinion dated Oct. 17, 2008 for International Application No. PCT/US2008/061451, filed Apr. 24, 2008 (7 pages).

International Search Report and Written Opinion dated Oct. 4, 2007 for International Application No. PCT/US05/37730, filed Oct. 20, 2005 (5 pages).

Office Action dated Feb. 12, 2010 for Chinese Patent Application No. 200580043930.4 (12 pages).

Office Action dated Mar. 17, 2010 for Japanese Patent Application No. 2006-515173 (4 pages).

Office Action dated Nov. 20, 2009 for Chinese Patent Application No. 200480021343.0 (25 pages).

Office Action dated Oct. 22, 2010 for Canadian Patent Application No. 2,528,417 (3 pages).

International Search Report and Written Opinion dated Apr. 28, 2011 for International Application No. PCT/US2010/046874, filed Aug. 26, 2010 (6 pages).

El-Tonsy, M.N., et al., "Continuous-wave Nd:Yag laser hyperthermia: a successful modality in treatment of basal cell carcinoma," Dermatology Online Journal, 10(2):12 pages, Oct. 2004.

(56) References Cited

OTHER PUBLICATIONS

Goldberg, S.N., et al., "Thermal ablation therapy for focal malignancy: a unified approach to underlying principles, techniques, and diagnostic imaging guidance," AJR American Journal Roentgenology, 174(2):323-331, Feb. 2000.

James, A., et al., "Airway smooth muscle in health and disease; methods of measurement and relation to function," The European Respiratory Journal, 15(4):782-789, Apr. 2000.

Lucroy, M.D., et al., "Selective laser-induced hyperthermia for the treatment of spontaneous tumors in dogs," Journal of X-Ray Science and Technology, 10(3-4):237-243, (2002).

Miller, J.D., et al., "A Prospective Feasibility Study of Bronchial Thermoplasty in the Human Airway," Chest, 127 (6):1999-2006, Jun. 2005.

Nikfarjam, M., et al., "Interstitial laser thermotherapy for liver tumours," British Journal of Surgery, 90(9):1033-1047, Sep. 2003.

Tearney, G., et al., "In Vivo Endoscopic Optical Biopsy with Optical Coherence Tomography," Science, 276 (5321):2037-2039, Jun. 1997.

Tumlinson, A., et al., "Endoscope-tip interferometer for ultrahigh resolution frequency domain optical coherence tomography in mouse colon," Optics Express, 14(5):1878-1887, Mar. 2006.

Vakhtin, A.B., et al., "Common-Path Interferometer for Frequency-Domain Optical Coherence Tomography," Applied Optics, 42(34):6953-6958, Dec. 2003.

Yun, S., et al., "Comprehensive volumetric optical microscopy in vivo," Nature Medicine, 12(12):1429-1433, Nov. 2006.

Ziemann, V., et al., "Ideas for an interferometric thermometer," Nuclear Instruments and Methods in Physics Research Section A: Accelerators, Spectrometers, Detectors and Associated Equipment, 564(1):587-589, Aug. 2006.

\* cited by examiner

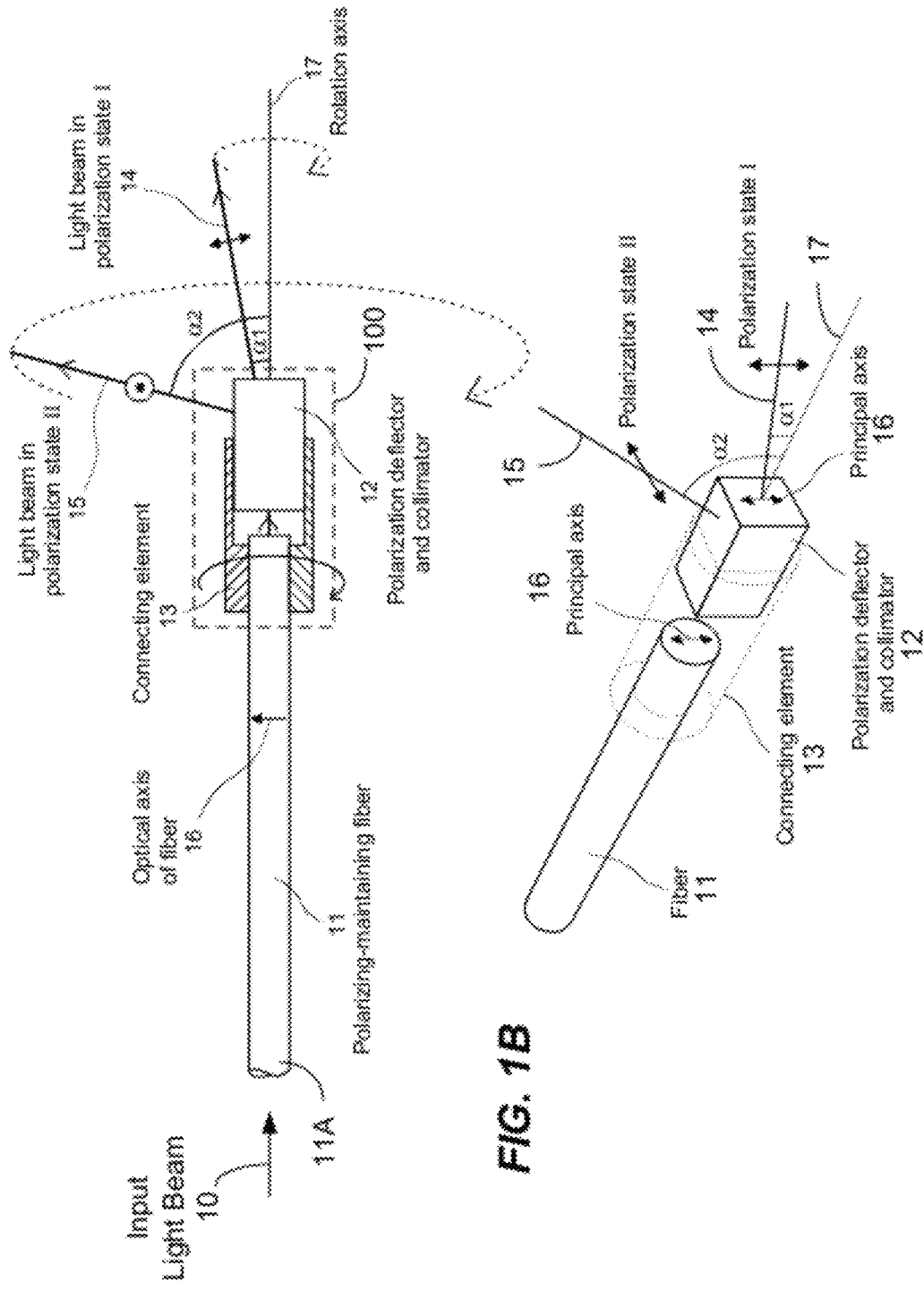

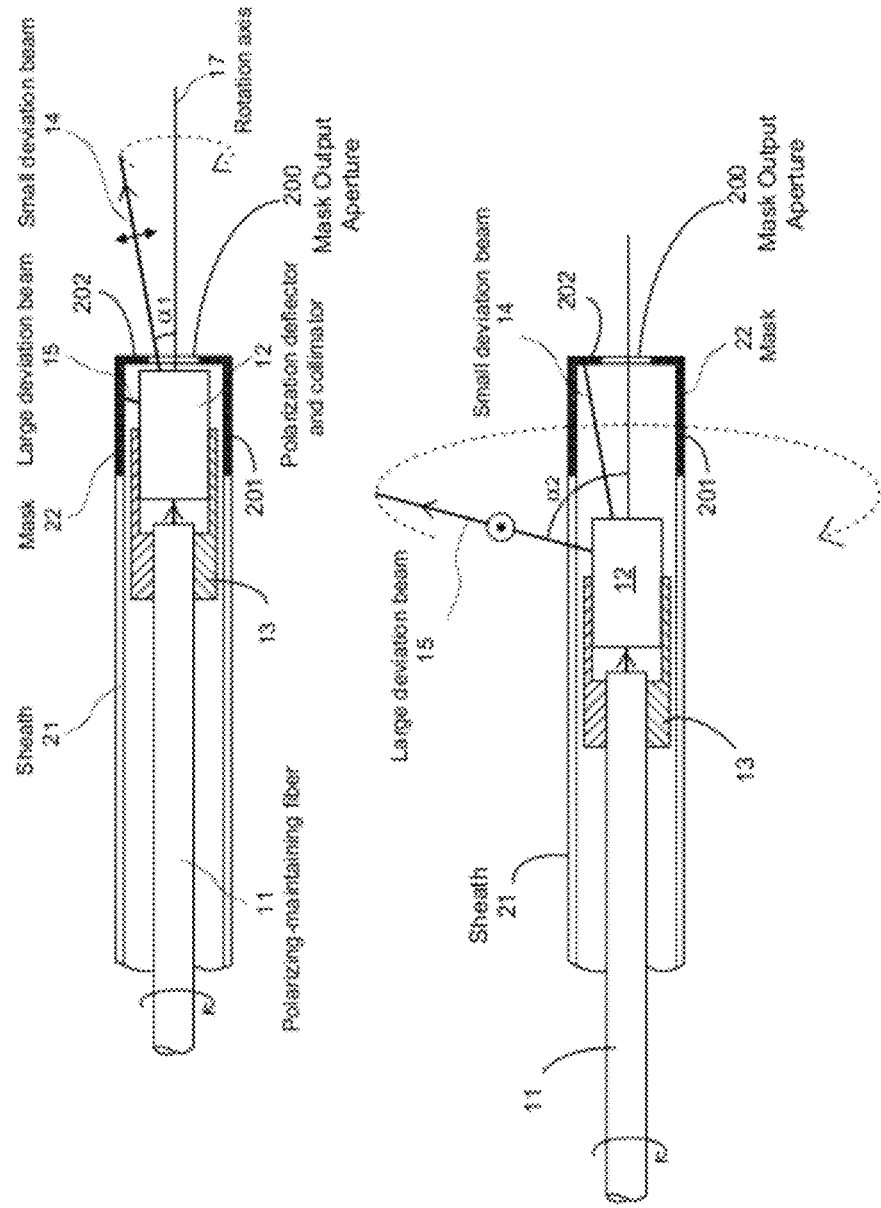

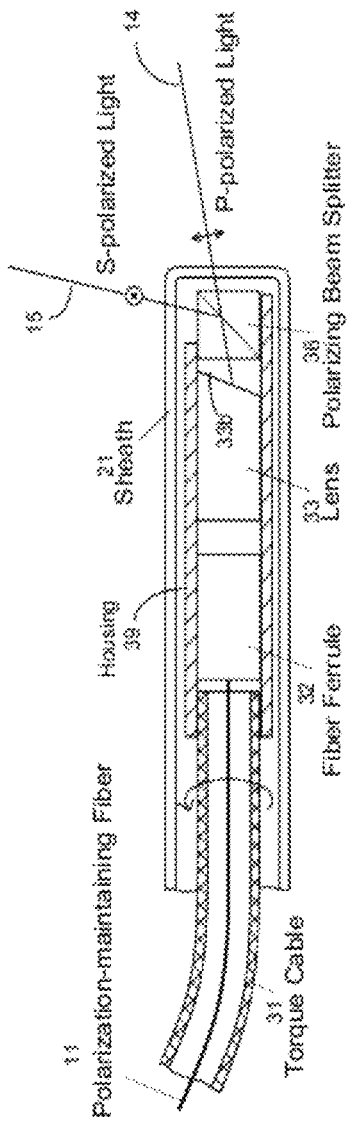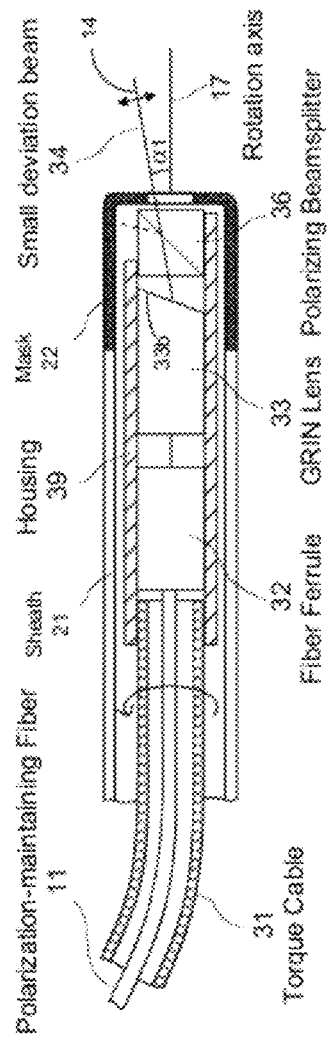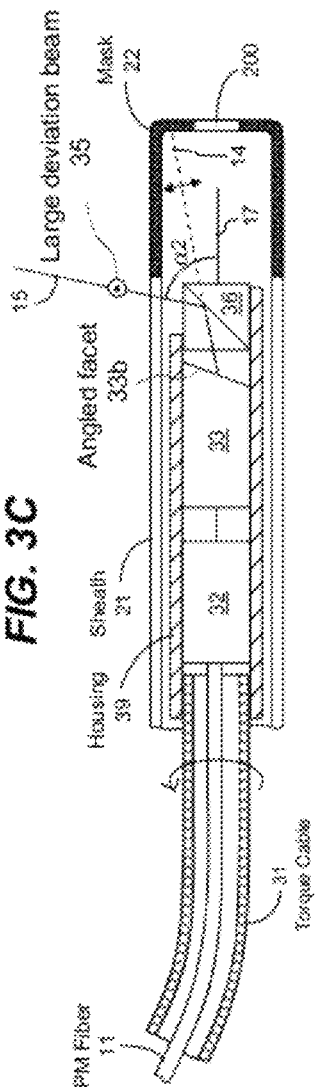
FIG. 3A
FIG. 3B
FIG. 3C

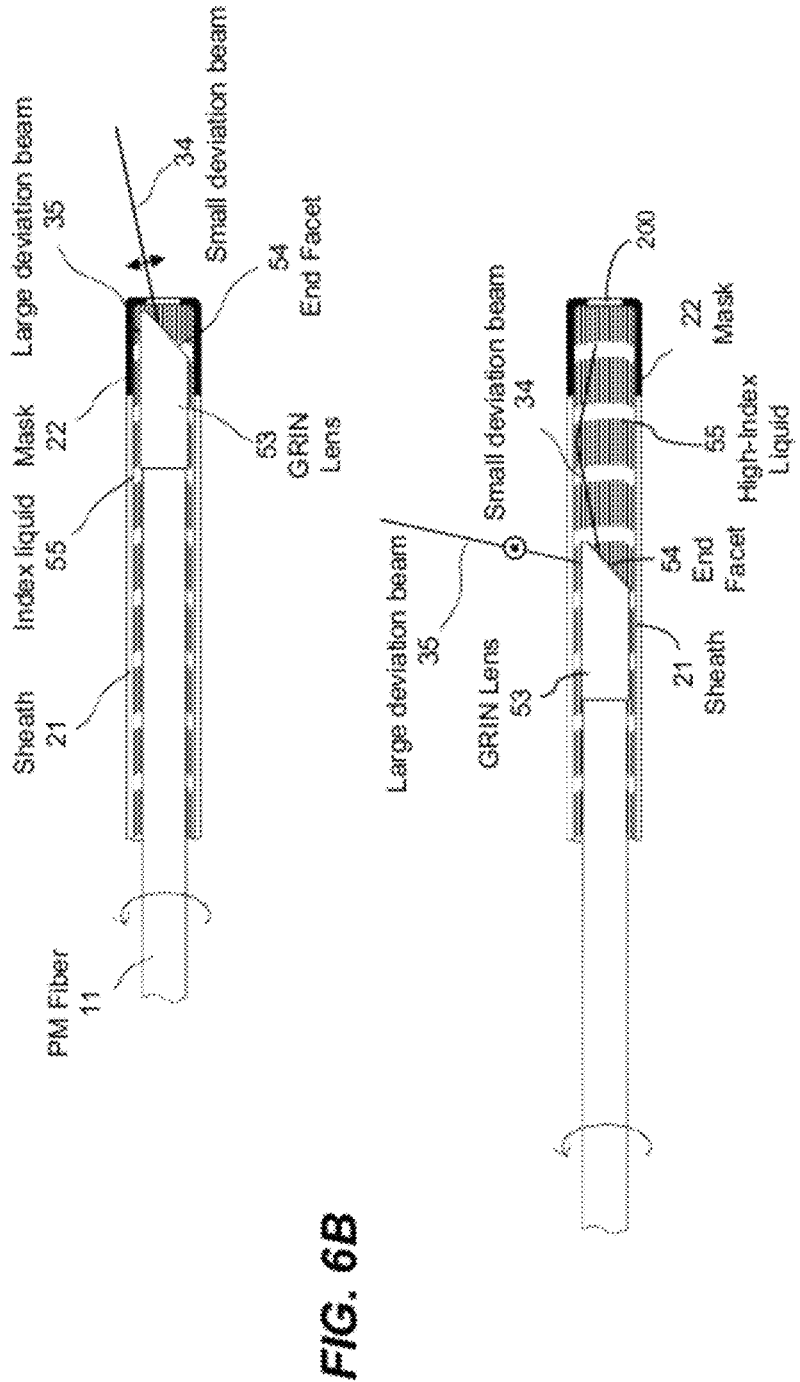

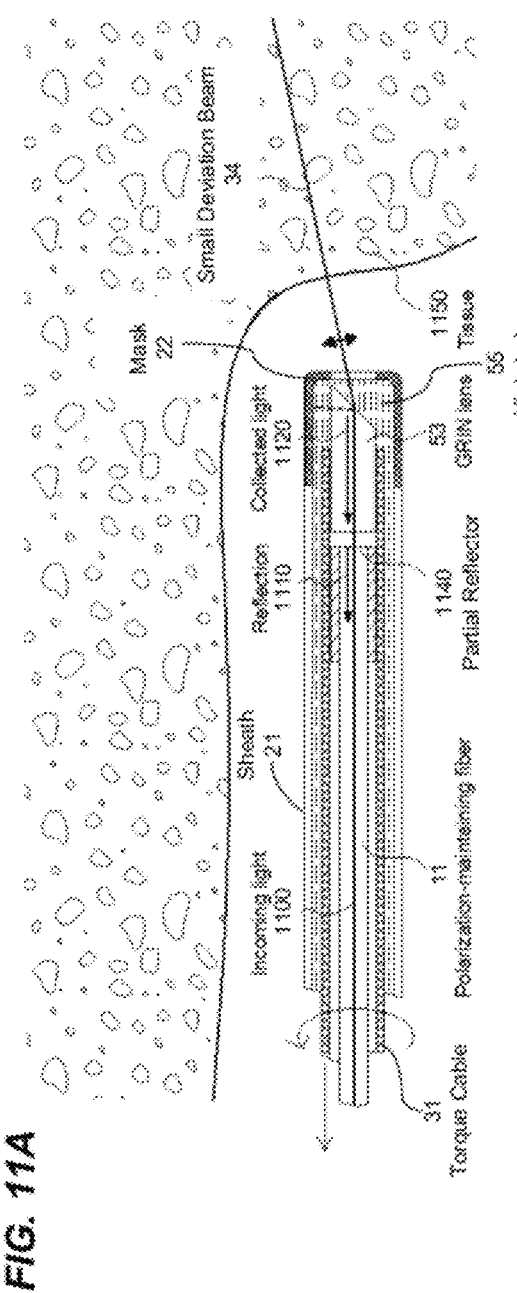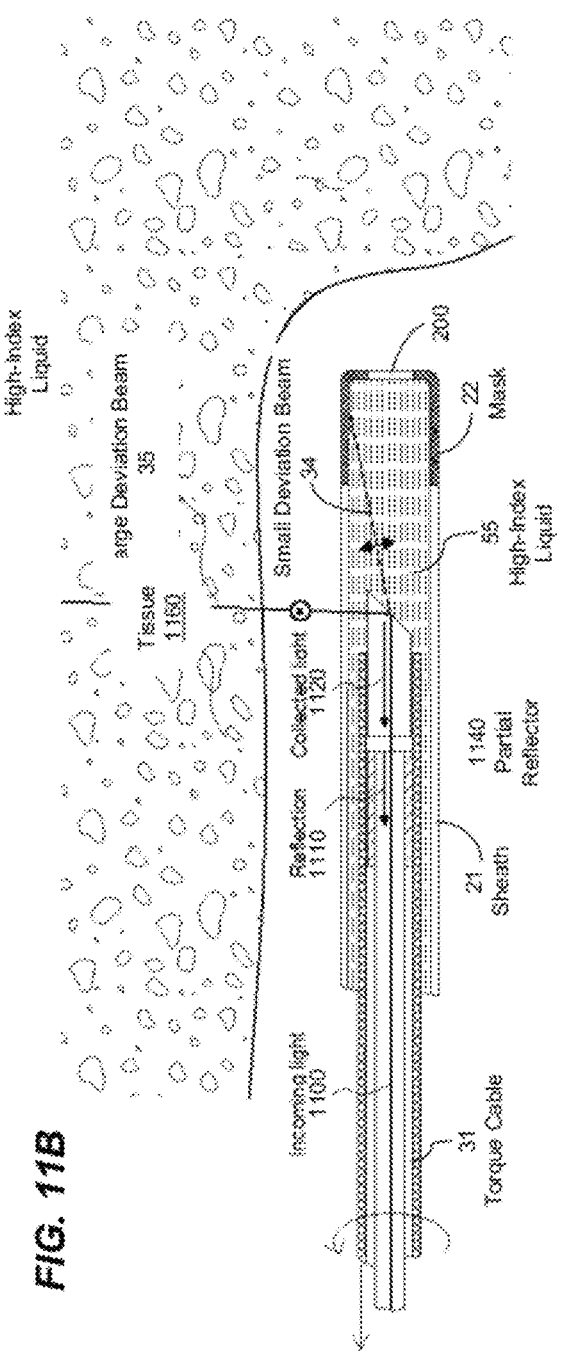

DELIVERING LIGHT VIA OPTICAL WAVEGUIDE AND MULTI-VIEW OPTICAL PROBE HEAD

CROSS-REFERENCE TO RELATED APPLICATIONS

This application is a continuation application and claims priority to U.S. patent application Ser. No. 12/767,729, filed Apr. 26, 2010, which is a divisional of U.S. patent application Ser. No. 12/075,129, filed Mar. 7, 2008, now U.S. Pat. No. 7,706,646, which claims benefit of U.S. Provisional Application No. 60/913,768, filed Apr. 24, 2007. The disclosures of the prior applications are considered part of (and are incorporated by reference in) the disclosure of this application.

BACKGROUND

This application relates to techniques, apparatus and systems that use optical waveguides to deliver light in endoscopes and other instrument for medical, biological, chemical and other applications.

Light can be guided through a light pipe or optical waveguide such as optic fiber to a target to obtain optical images, optical measurements and other operations of the target. The optical waveguide such as optic fiber can be used to reach the target at a location that is otherwise difficult to reach or requires some preparatory procedures to make the target more accessible. For example, the tissue of an internal organ of a patient may be made available for a medical examination or therapy procedure through a natural orifice or an incision to expose the internal organ. Such a procedure may be performed by delivering probe light to the tissue via an endoscope instrument or catheter to reduce or minimize the degree of invasiveness. At the distal end of the instrument, light is pointed to certain direction or steered to interact with an area or a slice of tissue of interest. Delivery of light via an optical waveguide can be implemented to perform various procedures, such as medical imaging, diffuse-reflection spectroscopy, fluorescence spectroscopy, coherence-gated optical tomography, photodynamic therapy, laser hyperthermia and others.

In the above and other procedures that direct light to a target issue, the light beam at the distal end of an endoscope instrument or catheter may be scanned to change the direction of the light beam and, in some procedures, it may be desirable to scan the light beam in more than one trajectory on the target tissue. Scanning of the light beam can be technically difficult because of various limitations in such applications imposed by locations, conditions, geometries, dimensions, or a combination of two or more of these and other factors associated with the target tissue. For example, in some procedures performed in vascular and pulmonary organs, the size of the channels, for instance, blood vessels or bronchus, may limit the dimensions of the instrument to sub-millimeters in their cross-sections and thus present a considerable challenge to designs of beam pointing or steering mechanisms.

SUMMARY

This application includes implementations and examples of techniques, apparatus and systems that use an optical probe head to deliver light to a target and to collect light from the target for imaging, monitoring, medical diagnostics and medical treatment applications. Described examples include optical probe scanners that, at a selected location, optically vary an angle of view of a scanning beam inside channels and cavities accessible through small instrument such as endoscopes, catheters and guidewires to obtain optical measurements of a target inside channels or cavities.

In one aspect, a device for delivering light to and collecting light from a target includes a sheath structured to include a hollow channel along a sheath longitudinal direction, the sheath having a proximal end configured to receive input polarized light and a distal end configured to export the input polarized light as probe light outside the sheath to a target; a polarization maintaining (PM) fiber movably placed inside the hollow channel of the sheath and structured to exhibit a first principal polarization direction and a second, orthogonal principal polarization direction, both perpendicular to a longitudinal direction of the PM fiber; and an optical probe head located inside the sheath and engaged to a distal end of the PM fiber with a fixed orientation relative to the first principal polarization axis of the PM fiber to receive the input polarized light from the PM fiber. The optical probe head is operable to direct the probe light polarized in the first principal polarization direction to exit the optical probe head at a first exit angle with respect to the sheath longitudinal direction and the probe light polarized in the second principal polarization direction to exit the optical probe head at a second, different exit angle with respect to the sheath longitudinal direction, respectively. This device includes a rotation mechanism coupled to the optical head and operable to rotate the optical head inside the sheath about the sheath longitudinal direction to change a direction of light existing the optical probe head at the first exit angle and at the second exit angle.

In another aspect, a method for delivering light via polarization-maintaining fiber to a target at two different trajectories includes controlling a state of polarization of light that is transmitted from a proximal end of a polarization-maintaining fiber to a distal terminal of the fiber; using polarization deflecting optics engaged to the distal end of the fiber to separate the light into a first beam in a first polarization by a first deflection angle and a second beam in a second polarization by a second deflection angle that is different from the first deflection angle; and rotating the polarization deflecting optics and the fiber together about a longitudinal axis of the fiber to cause the first beam in the first polarization to scan in a cone formed by the first deflection angle and the second beam in the second polarization to scan in a cone formed by the second deflection angle.

In yet another aspect, a method for optically interacting with a target includes directing probe light from a proximal terminal of a polarization-maintaining fiber to a distal terminal of the fiber to interact with a target at or near the distal terminal of the fiber; splitting the probe light at the distal terminal of the fiber into a first beam in a first principal polarization of the fiber propagating at a first deviation angle with respect to the fiber and a second beam in a second principal polarization of the fiber propagating at a second deviation angle that is different from the first deviation angle; controlling polarization of the probe light entering the proximal terminal of the fiber to be at the first principal polarization of the fiber to maximize optical power, at the distal terminal of the fiber, in the first beam while suppressing optical power in the second beam; and directing the first beam to reach a first region of the target while blocking the second beam from reaching a second region of the target that is different from the first region.

These and other aspects of various techniques, apparatus and systems are described in detail in the drawings, the description and the claims.

BRIEF DESCRIPTION OF THE DRAWINGS

FIGS. 1A and 1B illustrate one example of a dual-view optical probe head that produces forward-looking and side-looking views of a target based on two different polarizations of the light beam received by the optical probe head.

FIGS. 2A and 2B illustrate one implementation of the dual-view optical probe head design in FIGS. 1A and 1B movably placed inside a sheath and a mask at the distal end of the sheath to allow for selectively outputting light in one polarization while blocking residual light in the other orthogonal polarization.

FIGS. 3A, 3B, 3C, 4A, 4B, 5A, 5B, 6A and 6B illustrate additional exemplary implementations of the dual-view optical probe head design in FIGS. 1A and 1B, where a high-index liquid for controlling beam shape and creating a total internal reflection at an interior interface of a hollow channel within a sheath is used in FIGS. 5A, 5B, 6A and 6B.

FIGS. 11A and 11B show one example of an optical probe head capable of the dual-view operation as described in FIGS. 1A and 1B and generating a portion of light that does not reach the sample in the optical probe head for detection based on optical differential delay modulation.

(see explanation in the body text)

Figure 14:
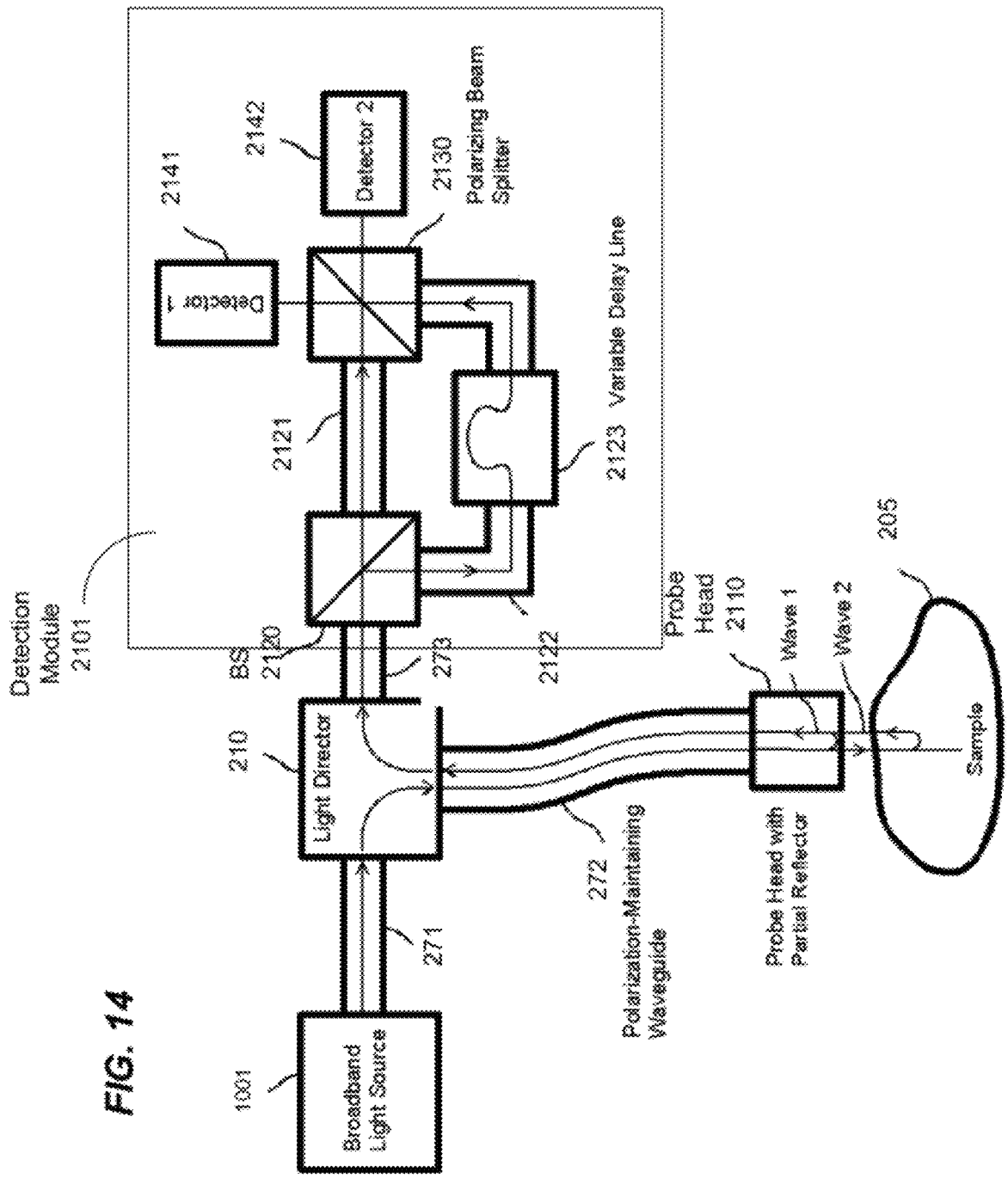

FIG. 14 illustrates another exemplary optical probe system for acquiring images of a target using a dual-view optical probe head design based on the design in FIGS. 11A and 11B.

Figure 15:
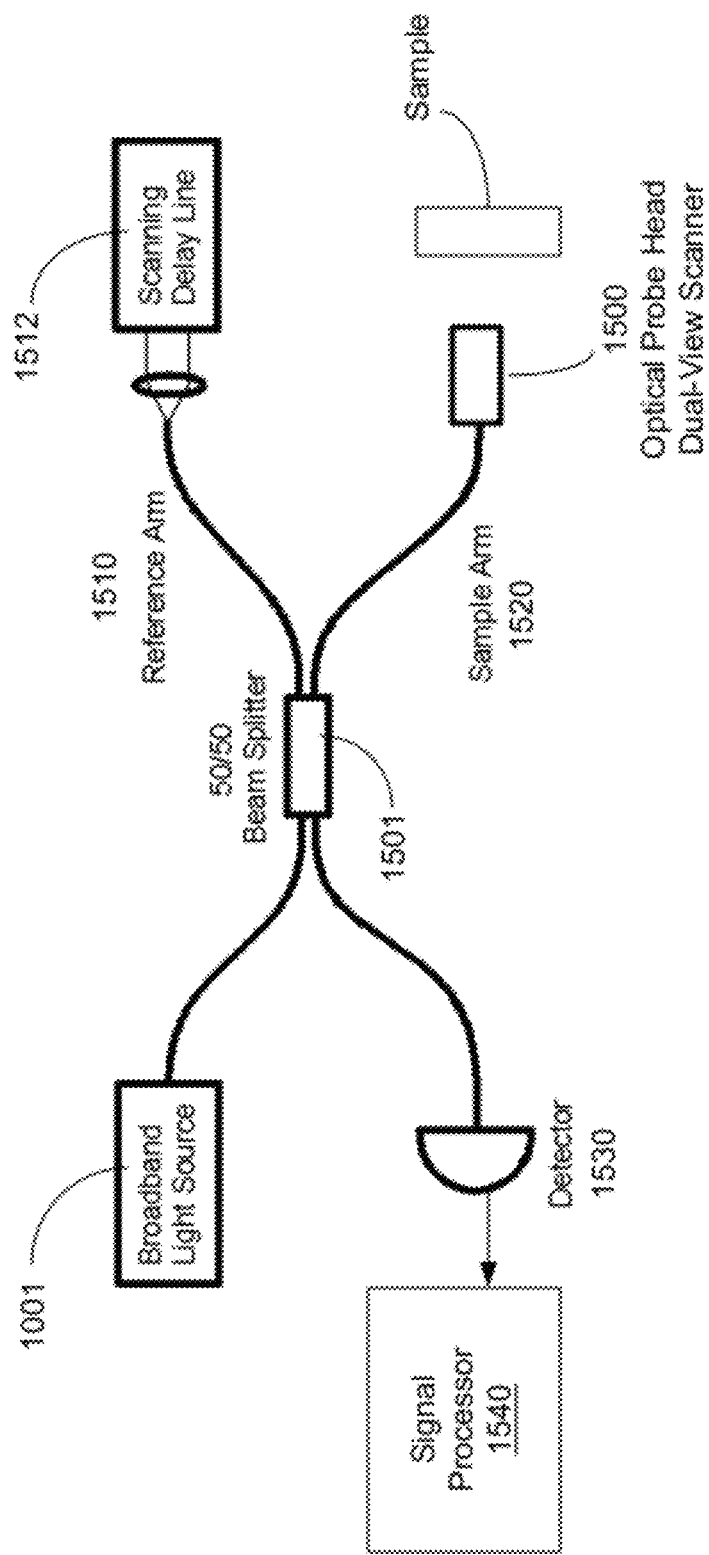

FIG. 15 illustrates an exemplary optical probe system for acquiring images of a target using a dual-view optical probe head design based on the design in FIGS. 1A and 1B and a Michaelson interferometer optical layout having an optical reference path to provide an optical reference beam and a sample optical path to provide an optical probe beam to interact with a sample.

Figure 16:
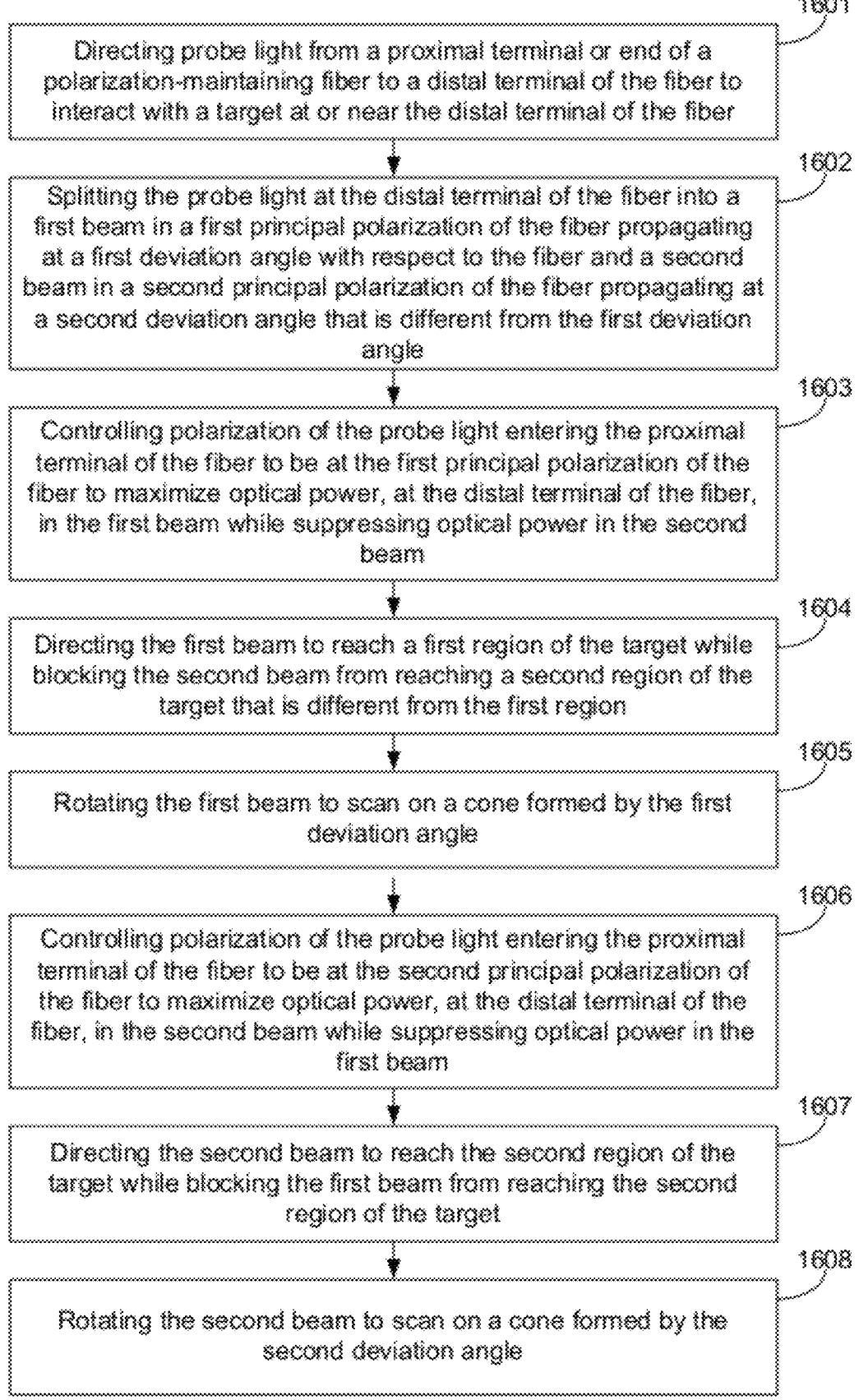

FIG. 16 shows one example of operations using one implementation of described techniques for delivering light to a target.

DETAILED DESCRIPTION

Implementations and examples described in this application for techniques, apparatus and systems that deliver light in endoscopes and other instrument designs via optical waveguides use optical polarization of the light guided in a polarization-maintaining (PM) optical waveguide to direct light in a first optical polarization along a first trajectory and to direct the light in a second optical polarization along a second, different trajectory. The optical probe head that produces the first and the second trajectories is engaged to the distal end of the optical waveguide and is configured to make the first trajectory along or at a small angle with respect to a longitudinal direction of the optical waveguide (e.g., to produce a forward-looking view of the target) and the second trajectory at a large angle with respect to a longitudinal direction of the optical waveguide (e.g., to produce a side-looking view of the target). The optical probe head 100 can include polarization deflecting optics, such as one or more polarization splitting components, to split light in the first and second polarizations along the first and second trajectories, respectively. The polarization of the light beam can be controlled to direct the light beam in either or both of the first and second trajectories. The polarization control mechanism can be, in one implementation, located outside the optical probe head such as a proximal end of the optical waveguide to simplify the structure of the optical probe head at the distal end of the optical waveguide. The assembly of the optical head and the optical waveguide, as an integral unit, can be rotated about a longitudinal axis of the optical waveguide so that the light beam in the first polarization rotates on a first cone surface around the optical waveguide and the light beam in the second polarization rotates on a second, different cone surface.

Therefore, both forward-looking and side-looking views of the target are provided in the implementations and examples described in this application and enable selection of either or both of the two different areas of the target for optical imaging, optical measurements or optical treatment. The designs of the implementations and examples described in this application can be used in various devices, such as endoscopes, catheters and guidewires, to obtain optical measurements (e.g., spectral absorption measurements) or images (e.g., cross-sectional or three-dimensional luminal images), or to perform optical treatment, of a target, such as a tissue or organ inside channels or cavities.

FIGS. 1A and 1B illustrate one example of an optical probe head 100 that produces the forward-looking and side-looking views of a target based on two different polarizations of the light beam received by the optical probe head. This optical probe head 100 is used as part of an instrument for delivering light to the target to conduct one or more optical operations, such as medical imaging, diffuse-reflection spectroscopy, fluorescence spectroscopy, coherence-gated optical tomography, photodynamic therapy, laser hyperthermia and others. A polarization-maintaining (PM) optical waveguide 11, such as a PM fiber, is provided to guide and direct an input light beam 10 from a proximal end 11A of the fiber 11 to a distal end 11B of the fiber 11. The fiber 11 is elongated along a longitudinal axis 17 and has a principal polarization axis 16 that is perpendicular to the longitudinal axis 17. The PM fiber 11 is optically birefringent along the principal axis 16 and another principal axis that is perpendicular to the axis 16 and the longitudinal axis 17 so that light in a polarization along with one of these two principal axes is maintained as the light propagates along the PM fiber 11. The optic axis of a birefringent material for the PM fiber 11, in one implementation, can be along the axis 16. The primal end 11A of the PM fiber 11 is coupled to other part of an instrument or device where a light source such as a laser is located to produce the input light beam 10. The distal end 11B is coupled to an optical probe head 100 that includes a polarization deflector unit 12 and a connector 13 that connects the polarization deflector unit 12 to the distal end 11B of the PM fiber 11. The connector 13 can include an a distal or frontal end 13A that is engaged to and holds the polarization deflector unit 12 and a proximal or rear end 13B that engages to the exterior part of the distal end 11B of the PM fiber 11. The fiber end facet of the distal end 11B outputs light to the polarization deflector unit 12 and receives returned light that is collected by the polarization deflector unit 12 from the target. The polarization deflector unit 12 directs light in a first polarization along the principal axis 16 of the PM fiber 11 so that it exits to become an output light beam 14 along the longitudinal axis 17 or at a small deflection angle 1 with respect to the axis 17 to provide a forward-looking view of the target area. The polarization deflector unit 12 also directs light in a second polarization perpendicular to the principal axis 16 of the PM fiber 11 so that it exits to become an output light beam 15 at a large deflection angle 2 with respect to the axis 17 to provide a side-looking view of the target area. The polarization deflector unit 12 can also be configured to collimate the output light beam 14 or 15 and to collimate light collected from a target area which is coupled into the distal end 11B of the PM fiber 11 and is detected at a proximal location.

The above dual angle-of-view beam scanner optical probe head 100 is reciprocal for light waves. Light originated in the path of the small deviation beam along the trajectory 14 can propagate from the distal location of the PM fiber 11 to the proximal location of the PM fiber 11 and can maintain its polarization, provided that the light is collected by the distal optics. This reciprocity equally exits in the large deviation beam along the trajectory 15. This reciprocity of the optical probe head 100 can be used in imaging or other optical modalities in which light is collected from the tissue in vivo and sent back to the proximal location for processing or analysis.

The polarization-maintaining optical waveguide 11, which is shown as a PM fiber in the example in FIGS. 1A and 1B, can be used to transmit light from the proximal location 11A to the distal location 11B with a controlled polarization state. This design can be used to align the polarization direction of the light at the distal end 11B to a particular direction so that the polarization deflector unit 12 can produce an output beam along one of the two trajectories 14 and 15. The control and switching of the polarization state of light can be implemented at the proximal location 11A to control the polarization of the light at the distal location 11B to select either an area in front of the optical probe head 100 in the path of the output light beam 14 or an area on the side of the optical probe head 100 in the path of the output light beam 15 for interrogation of tissues with the single optical probe head 100.

The polarization deflector unit 12 may include one or more polarizing optical elements to deflect light in the first polarization along the first trajectory 14 and light in the second polarization along the second trajectory 15. In practical devices, light in these two different polarizations may not be completely separated based on the polarization at the output of the optical probe head 100. This condition may be caused by, e.g., the presence of some residual amount of light in the first polarization at the polarization deflector unit 12 when the light is controlled at the proximal end 11A to be in the second polarization or vice versa, or the operation of the polarization deflector unit 12 which may produce some residual amount of light in the first trajectory 14 when the light received from the PM fiber 11 is in the second polarization or vice versa. This presence of a residual amount of light in one trajectory when the optical probe head 100 is operated to direct the light beam in the other trajectory mixes returned light from the two different target areas and makes it difficult to process the returned light to obtain information on one of the two different target areas. For example, in an imaging instrument using such an optical probe head 100 to obtain images along a selected trajectory, the presence of a residual amount of light in the other un-selected trajectory can cause the optical probe head 100 to receive returned light from the target in both trajectories 14 and 15 and thus cause undesired overlapping and mixing of images from two different areas of the target in the returned light. Similarly, this mixing of light in two trajectories is also undesirable in devices using the optical probe head 100 for non-imaging applications.

One approach to mitigating this technical issue is to provide a mechanism to allow the output beam to reach the target along one selected trajectory while selectively blocking light from reaching the target along the other, non-selected trajectory. In one implementation, a sheath is structured to include a hollow channel as a housing for the PM fiber 11 and the optical probe head 100 and a mask formed on the distal end of the sheath to form a spatial filter that blocks light in either one of the two trajectories 14 and 15 while allowing light in the other trajectory to reach the target. The position of the optical probe head 100 with respect to the distal location of the sheath along the axis 17 is controlled to select light along one of the two trajectories 14 and 15 to reach the target.

FIGS. 2A and 2B illustrate an example of an optical probe head that incorporates a sheath with a mask to block unwanted residual light in one trajectory based on the design in FIGS. 1A and 1B. The sheath 21 is structured to include a hollow channel along a sheath longitudinal direction which is parallel to or coincides with the rotation axis 17. The interior of the hollow channel is sized to receive and movably hold the optical probe head 100 and the PM fiber 11 engaged to the optical probe head 100. The optical probe head 100 and the PM fiber 11 can be pulled or pushed to move along the hollow channel of the sheath 21 to change the position of the optical probe head and thus the polarization deflector unit 12 along the rotation axis 17. The sheath 21 is formed of a material that transmits the light guided by the PM fiber 11.

A mask 22 is formed at the distal end of the sheath 21 and shaped like barrel to have an output aperture 200. The mask 22 allows for transmission of light along the trajectory 15 through the side surfaces of the sheath 21 that is not blocked by the mask and allows for transmission of the light along the trajectory 14 through the output aperture 200. The optical probe head 100 and the PM fiber 11 engaged to the optical probe head 100 can be moved along the hollow channel of the sheath 21 to one or more first positions at which the light beam in the first polarization along the first trajectory 14 transmits through the output aperture 200 of the mask 22 while the light beam in the second polarization along the second trajectory 15 is being blocked by the mask 22. FIG. 2A illustrates one such example. The optical probe head 100 and the PM fiber 11 engaged to the optical probe head 100 can also be moved along the hollow channel of the sheath 21 to one or more second positions at which the light beam in the second polarization along the second trajectory 15 transmits through a side surface of the sheath 22 that is not covered by the mask 22 while the light beam in the first polarization along the first trajectory 14 is being blocked by the mask 22. FIG. 2B illustrates one such example. The one or more second positions are further away from the distal end facet of the sheath 21 than the one or more first positions. At either the first or second positions, the optical probe head 100 and the PM fiber 11 engaged to the optical probe head 100 can be rotated about the rotation axis 17 to scan the unblocked output over the target along the trajectory 14 or 15 while the other beam being blocked by the mask 22.

The use of the mask 22 on the sheath 21 in FIGS. 2A and 2B can ensure that only one output beam in a selected trajectory out of the two trajectories 14 and 15 is directed to reach the target for imaging, sensing or optical treatment applications. Therefore, incomplete suppression of the light in the non-selected trajectory via the polarization control in the instrument can be tolerated because the residual light in the non-selected trajectory is blocked by the mask 22 when the optical probe head 100 is placed at a proper position so that all returned light is generated by the reflection and scattering of the light along the selected trajectory. This design can allow low quality beam splitters and other low quality polarization optical elements that poorly separate the two orthogonal polarizations to be used to construct the optical probe head 100 to reduce the material cost of the optical probe head 100.

Referring to FIGS. 1A and 1B, the optical probe head 100 is designed based on the use of the polarization deflector unit 12 to split light in the two orthogonal polarizations along two separate trajectories 14 and 15. Alternatively, with the masking sheath in FIGS. 2A and 2B, the optical probe head 100 can be replaced by an optical probe head that uses a non-polarizing optical beam splitter to substitute the polarization deflector unit 12. This non-polarizing beam splitter splits an input beam, regardless of its optical polarization, into a first output beam along the first trajectory 14 and a second output beam along the second trajectory 15 to interact with two different areas of the target. The position of the optical probe head 100 along the longitudinal direction of the hollow channel of the sheath 21 is adjusted to direct only one of the first and second output beams to the target while blocking the other output beam by the mask 22. In FIG. 2A, the optical probe head 100 is placed at a position close to the distal end of the sheath 21 so that the large deviation beam along the trajectory 15 is blocked by the mask 22 and the small deviation beam along the trajectory 14 transmits through the output aperture 200 at the end facet of the mask 22. In FIG. 2B, the optical probe head 100 is placed at a position away from the distal end of the sheath 21 so that the large deviation beam along the trajectory 15 misses the mask 22 and transmits through the side of the sheath 21 as an output beam whereas the small deviation beam along the trajectory 14 misses the output aperture 200 at the end facet of the mask 22 and is blocked by the mask 22. This design of the assembly of a non-polarizing optical probe head and can be combined with various features described in application.

The polarizing optical probe head 100 in FIGS. 1A and 1B can be implemented in various configurations. Several specific examples are described below.

FIG. 3A shows one implementation of the polarizing optical probe head 100 in FIGS. 1A and 1B. FIGS. 3B and 3C show two modes of operation of the probe head in FIG. 3A based on a mask formed at the distal end of the sheath. A fiber ferrule 32 is provided to hold the PM fiber 11 and a housing 39 is used to hold the fiber ferrule 32, a collimator lens 33, and a polarizing beam splitter 36. In this example, the connector 13 in FIGS. 1A and 1B is implemented by the housing 39 and the fiber ferrule 32; and the polarization deflector unit 13 is implemented collectively by the collimator lens 22 and the polarizing beam splitter (PBS) 36. The collimator lens 22 collimates the beam output by the fiber 11 and couples light collected from the target into the fiber 11. One example of the collimator lens 22 is a graded index (GRIN) lens commonly used in fiber optics. The distal end facet 33*b* of the GRIN lens 22 can be an angled facet with an acute angle with respect to a direction perpendicular to the rotation axis 17. This facet 33*b* and the orientation of the polarizing reflective surface of the PBS 36 can be designed to determine the directions of the two trajectories 14 and 15. The polarizing beam splitter 36 splits the light beam from the lens 33 into a first linear polarized beam 34 (e.g., P-polarized) along the first trajectory 14 and a second linear polarized beam (e.g., S-polarized) along the second trajectory 15.

In operation, the optical probe head 100 can be placed at a position close to the distal end of the sheath 21 (FIG. 3A) so that the large deviation beam along the trajectory 15 is blocked by the mask 22 and the small deviation beam 34 along the trajectory 14 transmits through the output aperture 200 at the end facet of the mask 22. Alternatively, the optical probe head 100 can be placed at a different position away from the distal end of the sheath 21 so that the large deviation beam along the trajectory 15 misses the mask 22 and transmits through the side of the sheath 21 as an output beam 35 while the small deviation beam 34 along the trajectory 14 is blocked by the mask 22.

In this particular example, a torque cable 31 is provided to hold the PM fiber 11 and is fixed to the proximal or rear end of the housing 39 so that the torque cable 310, the PM fiber 11 and the housing 39 along with the lens 33 and polarizing beam splitter 36 held by the housing 39 rotate together as a single assembly within the hollow channel of the sheath 21. A rotation mechanism is engaged to the torque cable 31 and operates to rotate the torque cable 31 so as to rotate the direction of each of the two output beams respectively propagating along the two trajectories 14 and 15 with respect to the target to optically interacting with different target regions or areas in the path of the rotating output beam. Referring to FIGS. 3B and 3C, the sheath 21 is designed to include the mask 22 at its distal end for blocking one of the two output beams respectively propagating along the two trajectories 14 and 15. The longitudinal position of the optical probe head 100 can be controlled by pushing or pulling the torque cable 31 to select one of the two output beams for interacting with the target while blocking the other output beam.

Figure 4A:
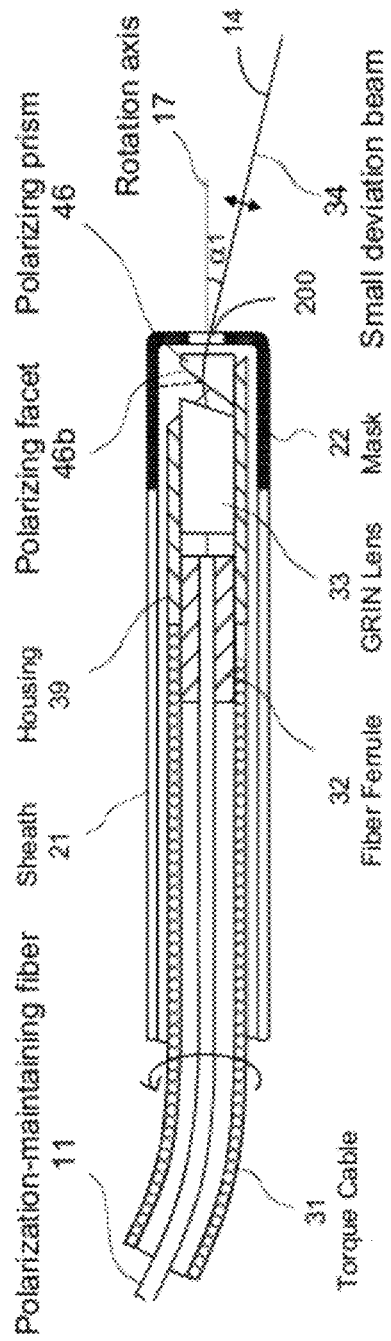
Figure 4B:
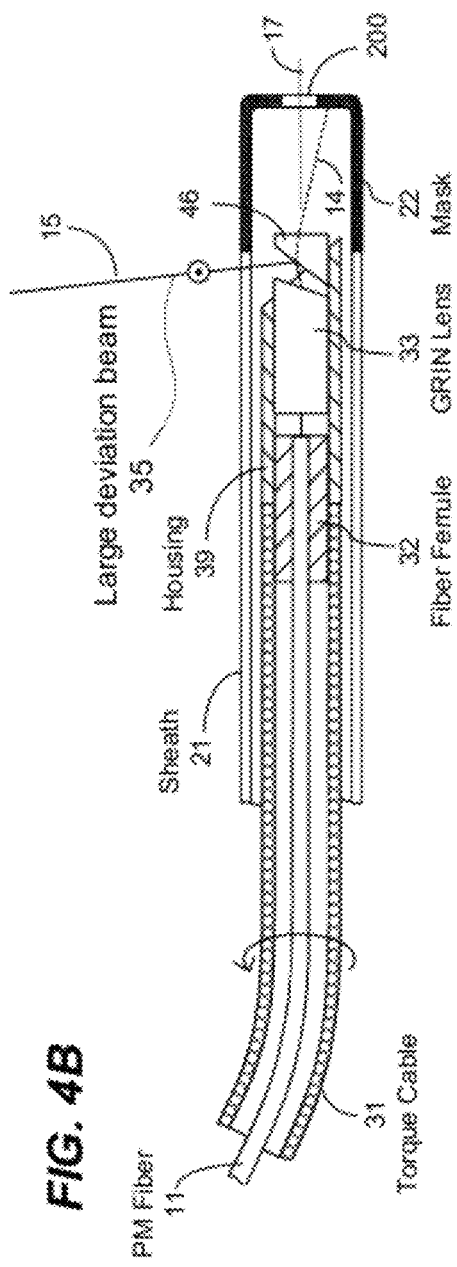

FIGS. 4A and 4B show another exemplary implementation of the optical probe head 100 where a polarizing prism 46 is used to substitute the PBS 36 in FIGS. 3A, 3B and 3C. The polarizing prism 46 has a polarizing facet 46*b* that faces the output facet 33*b* of the GRIN lens 33. The polarizing facet 46*b* diffracts light in the first polarization to transmit through the body of the polarizing prism 46 as the first output beam along the first trajectory 14 and reflects light in the second polarization along the second trajectory 15. This example also shows an alternative design for engaging the torque cable 31 the optical probe head where a portion of the fiber ferrule 32 protruded outside the proximal side of the housing 39 is directly engaged to the torque cable 31.

Figure 5A:
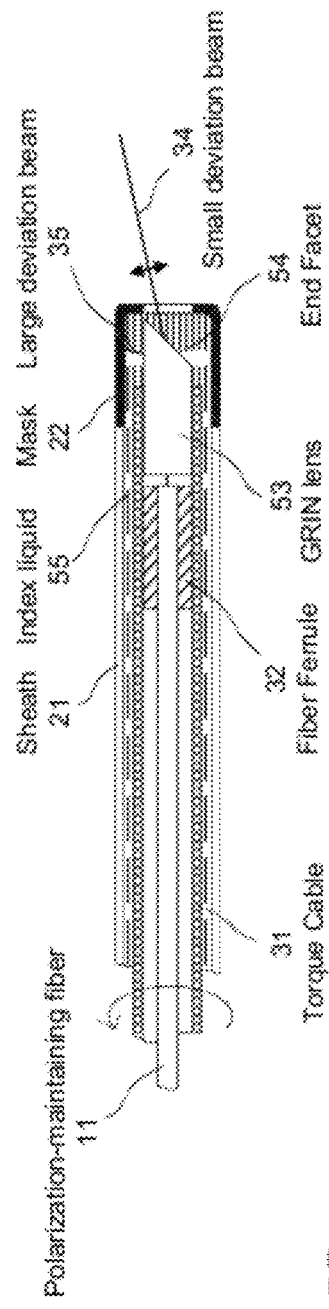
Figure 5B:
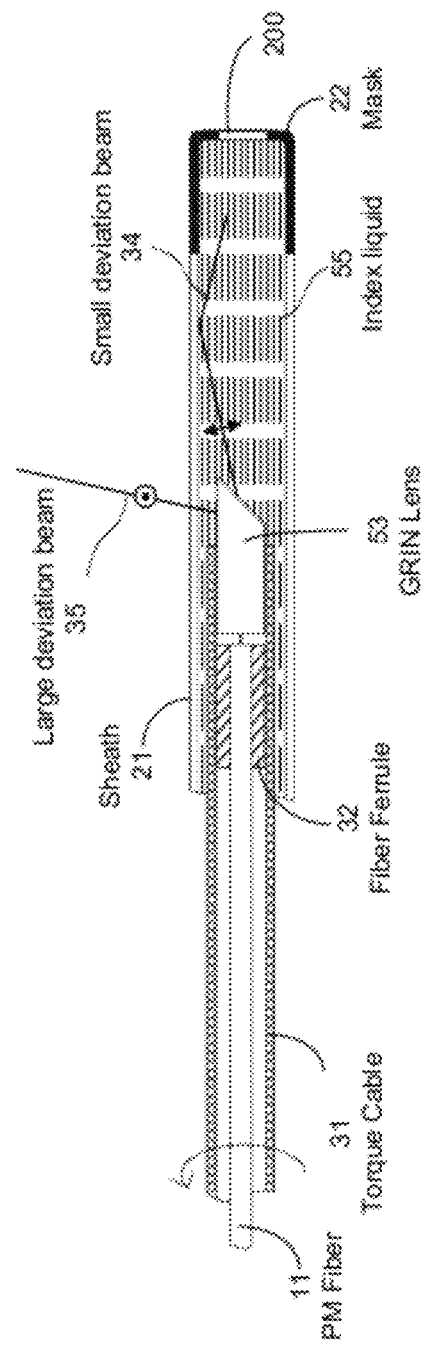

FIGS. 5A and 5B show an example where a GRIN lens 53 with an end facet 54 is used to provide both the optical collimation function and the polarization separation function. The end facet 54 is an angled facet and is coated with a multi-layer thin film stack that transmits light in the first polarization along the trajectory 14 and reflects light in the second polarization along the trajectory 15. Such a thin-film systems, deposited on angled surfaces, for preferentially transmitting and deflecting light according to the polarization are known and are readily available. See, e.g., "Handbook of Optics," M. Bass et al ed, McGraw-Hill (1995). Such thin film systems operate under the principle of optical interference produced by the interfaces in these multilayered structures. Due to the oblique incidence, light polarized in the incident plane is transmitted and reflected differently from light polarized perpendicularly to the incident plane.

Similar to other designs shown above, the optical probe head in FIGS. 5A and 5B is designed to have two modes of operation to select one of the two output beams with orthogonal polarizations. In FIG. 5A, the optical probe head 100 is placed at a position close to the distal end of the sheath 21 to block the large deviation beam along the trajectory 15 and to transmit the small deviation beam 34 along the trajectory 14 through the output aperture 200 to reach the target. In FIG. 5B, the optical probe head 100 is placed at a different position away from the distal end of the sheath 21 so that the large deviation beam along the trajectory 15 misses the mask 22 and transmits through the side of the sheath 21 as an output beam 35. Similarly to the positions of the optical probe head 100 in FIGS. 3C and 4B, the position of the optical probe head 100 in this design can be selected to be sufficiently close to the end facet of the sheath 21 so the small deviation beam 34 along the trajectory 14 is blocked by the mask 22.

The optical probe head 100 may also be placed at a position sufficiently far away from the distal end of the sheath 21 so that both the large deviation beam 35 along the trajectory 15 and the small deviation beam 34 along the trajectory 14 hit the side surface of the sheath and miss the mask 22. Under this condition, both beams 34 and 35 can transmit through the side surface of the sheath 21 to reach the target. This situation is undesirable and can be prevented by using a total internal reflection at the inner surface of the side of the sheath 21.

FIG. 5B illustrates one design for achieving such a total internal reflection of the small deviation beam 34 at the inner surface of the side of the sheath 21. In this example, the interior of the hollow channel of the sheath 21 is filled with a high index liquid 55 that has a refractive index greater than that of the sheath 21. This liquid 55 fills the space between the optical probe head 100 and the interior of the hollow channel of the sheath 21 so that the small deviation beam 34 along the trajectory 14, being at a smaller angle with respect to the axis 17 than the large deviation beam along the trajectory 15, can have an incident angle at the liquid-sheath interface to be greater than the critical angle for the total internal reflection and thus undergo a total internal reflection at the liquid-sheath interface. The angle of the angled end facet 54 of the GRIN lens 53, the refractive index of the liquid 55 and the refractive index of the sheath 21 can be selected to achieve the total internal reflection condition for the small deviation beam 34 while the large deviation beam 35 is incident at a side inner wall of the sheath 21 at an angle less than the critical angle for the total internal reflection. In addition to providing this optical total internal reflection, the liquid 55 can also serve as a lubricant between the inner side wall of the sheath 21 and the movable optical probe head 100 and can set an appropriate focusing effect for the large deviation beam caused by the lens-liquid interface. This use of a high-index liquid can also be used in other designs described in this application, including designs in FIGS. 2A, 2B, 3A, 3B, 3C, 4A and 4B.

FIGS. 6A and 6B show another example of an optical probe head where the PM fiber 11 is directly coupled to the GRIN lens 53 to transfer rotations from the proximal of the fiber 11 to the distal end of the fiber where the GRIN lens 53 is engaged. The PM fiber 11 can be bonded to the GRIN lens 53 by, e.g., fusion bonding or adhesive bonding. The PM fiber 11 may be chosen or designed to bear the mechanical twisting of the fiber during rotation. Polymer coatings can be deposited on glass fibers for enhancing their mechanical strength and for bearing a rotation torque applied to the PM fiber 11.

Figure 7:
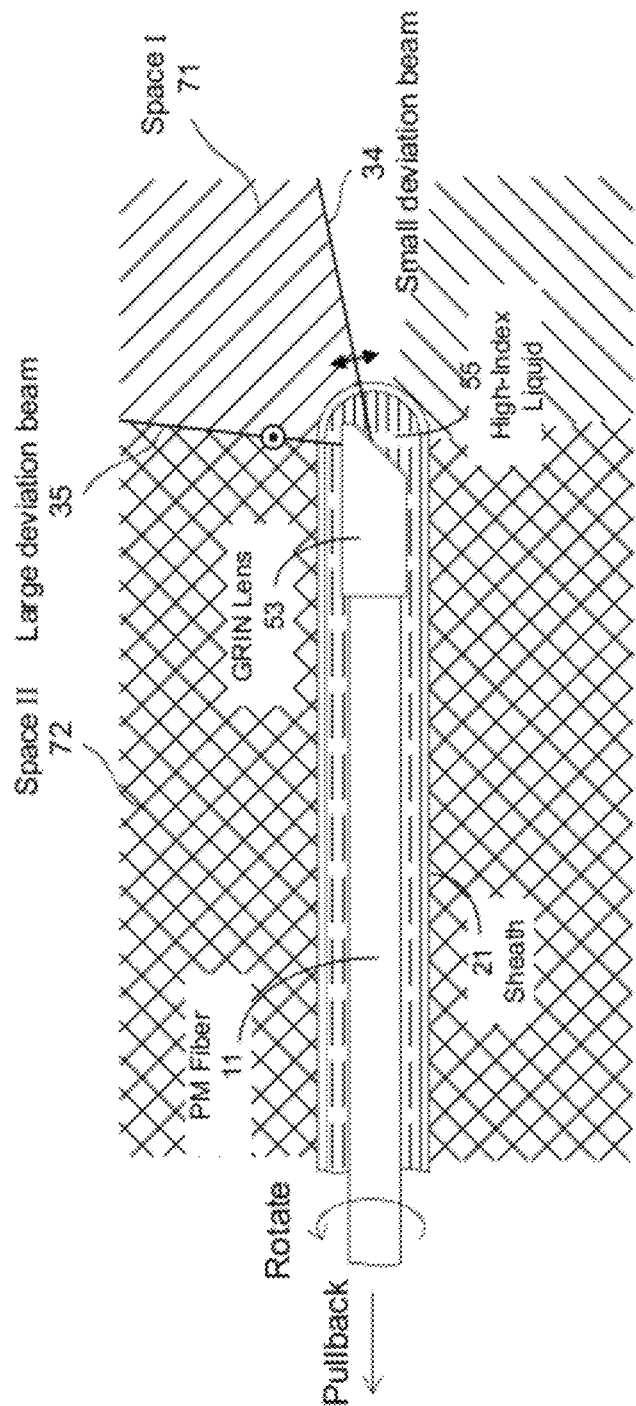
FIG. 7 illustrates regions of a target that are respectively accessible by two orthogonally polarized probe beams produced by an optical probe head based on the design in FIGS. 1A and 1B.

Referring to FIG. 7, the present optical probe head designs can be operated to slide the optical probe head 100 inside the sheath 21 along the sheath 21 to select one of the two beam trajectories 14 and 15 for interacting with the surrounding target by dividing the target area into a first region I (71) for interaction with the small deviation beam 34 along the trajectory 14 and a second region II (72) for interaction with the large deviation beam 35. In the region II, the optical probe head 100 is moved inside the sheath 21 to interact with different target areas within the region II throughout the length of the PM fiber 11. The rotation of the optical probe head 100 around the axis 17 allows the optical probe head 100 to interact with all target areas in the path of the rotating large deviation beam 35. When the optical probe head 100 is positioned to direct only the small deviation beam 34 into the target region I (71), the rotation of the optical probe head 100 allow the beam 34 to interact with all target areas in the path of the rotating small deviation beam 34 in the target region I (71). The combination of the translational motion and rotational motion of the optical probe head 100 allows for the interrogation of tissues in a space volume not entirely accessible with fixed-angle scanners.

In many devices using the optical probe head 100, the distal optics in the optical probe head 100 needs to rotate to interact with different target regions within the target at a given location of the optical probe head 100, e.g., obtaining images of tissues in all the accessible space. Winding up of unbroken optical fibers can limit the number of rotations in turning the distal optics in the optical probe head 100 and can also require rewinding. For uninterrupted and accurate tissue mapping and other applications, it is desirable to contiguously rotate the distal optics within the optical probe head 100 along one rotation direction and to reverse the rotation at any time without undergoing rewinding.

Figure 8:
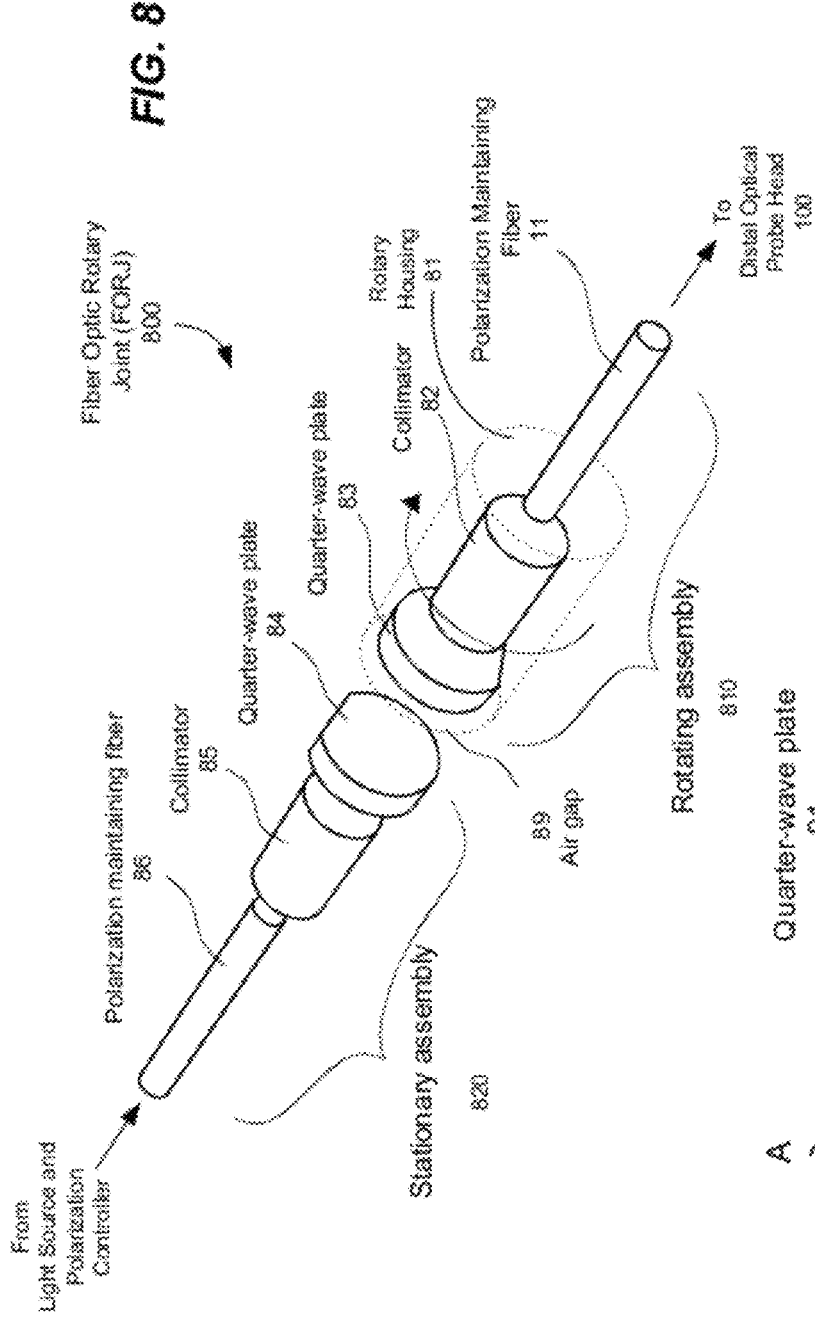
FIGS. 8 and 9 illustrate the design and operation of an air-spaced fiber optic rotary joint (FORJ) that can be used to provide contiguous rotations of the distal optics of the optical probe head while preserving a linear polarization state of light that passing through the FORJ.

FIG. 8 illustrates an example of an air-spaced fiber optic rotary joint (FORJ) 800 that can be used to provide contiguous rotations of the distal optics of the optical probe head 100.

The FORJ 800 includes a stationary assembly 820 that connects to a PM fiber 86 and a rotating assembly 810 that connects to the proximal end of the PM fiber 11 whose distal end is connected to the optical probe head 100. An air gap 89 separates the rotating assembly 810 from the stationary assembly 820 to allow the rotating assembly 810 to freely rotate with respect to the stationary assembly 820 around a rotation axis going through the center of the PM fiber 11. The FORJ 800 is designed to maintain light polarization in a principal direction of the optical fiber from the proximal end to the distal end through the FORJ 800.

The rotating assembly 810 includes a quarter wave plate 83 that interfaces with the air gap 89 to receive input light from the stationary assembly 820, and a collimator lens 82 (e.g., a GRIN lens) that collimates the light from the quarter wave plate 83. The collimator lens 82 is coupled to the proximal end of the PM fiber 11. The quarter wave plate 82, the collimator 82 and the proximal end of the fiber 11 are fixed in position relative to one another to move as an integral unit. A rotary housing 81 may be used to hold the quarter wave plate 83, the collimator 82 and the proximal end of the fiber 11 as a single unit and can be rotated together around the longitudinal axis of the fiber 11. Similarly, the stationary assembly 820 includes a collimator 85 (e.g., a GRIN lens) that connects to the distal end of the PM fiber 86, and a quarter wave plate 84 that is fixed to the collimator 85 in position to receive light from the collimator 85. The three elements 11, 82 and 83 in the rotating assembly 810 are held and integrated together in such a way that one principal axis of the PM fiber 11 makes a 45 degree angle with respect to a principal axis of the quarter-wave plate 83. The same relative orientation is maintained for the quarter-wave plate 84 and the PM fiber 86 in the stationary assembly 820.

Figure 9:
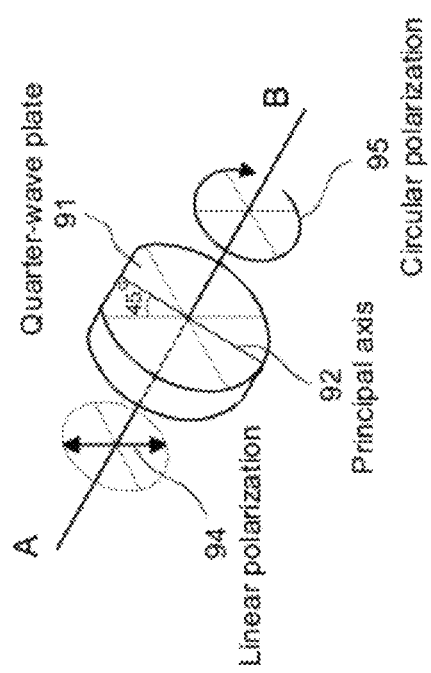

The preservation of the polarization from the PM fiber 86 to the PM fiber 11 through the FORJ 800 is accomplished through the conversion of polarization from a linear state in the transmitting fiber to a circular state in the air gap 89 and a conversion from the circular state on the other side of the air gap 89 back to a linear state again in the receiving fiber. FIG. 9 illustrates operation of each of the quarter-wave plates 83 and 84 where A represents output of PM fiber 86 or 11 with a linear polarization 94, and the quarter wave plate 91 represents the quarter wave plate 84 or 83 which converts the linear state of polarization 94 into a circular polarization state 95 in the air gap 89, and vice versa. The state of the circular polarization of the light in the air gap 89 ensures that the linear polarization states in the fibers 11 and 86 are irrespective of the orientation of the rotating assembly 810 relative to the stationary assembly 820. Therefore, the light maintains a linear polarization state in the PM fiber 81 while rotating.

The FORJ 800 can be implemented by using various quarter-wave plates. Some birefringence-based quarter-wave plates are manufactured from crystal quartz or other birefringent materials and tend to exhibit a substantial deviation from the quarter wave condition when the light wavelength deviates from the designed wavelength. Hence, when a broad wavelength range needs to be carried to and from the beam scanner optical probe head 100, achromatic wave plates may be used to maintain the quarter wave condition over the broad wavelength range. A Fresnel rhomb prism is one type of achromatic quarter-wave retarders that can maintain the quarter-wave condition for a broad wavelength range. Achromatic waveplates can also be formed by using two birefringent plates of different materials.

Figure 10:
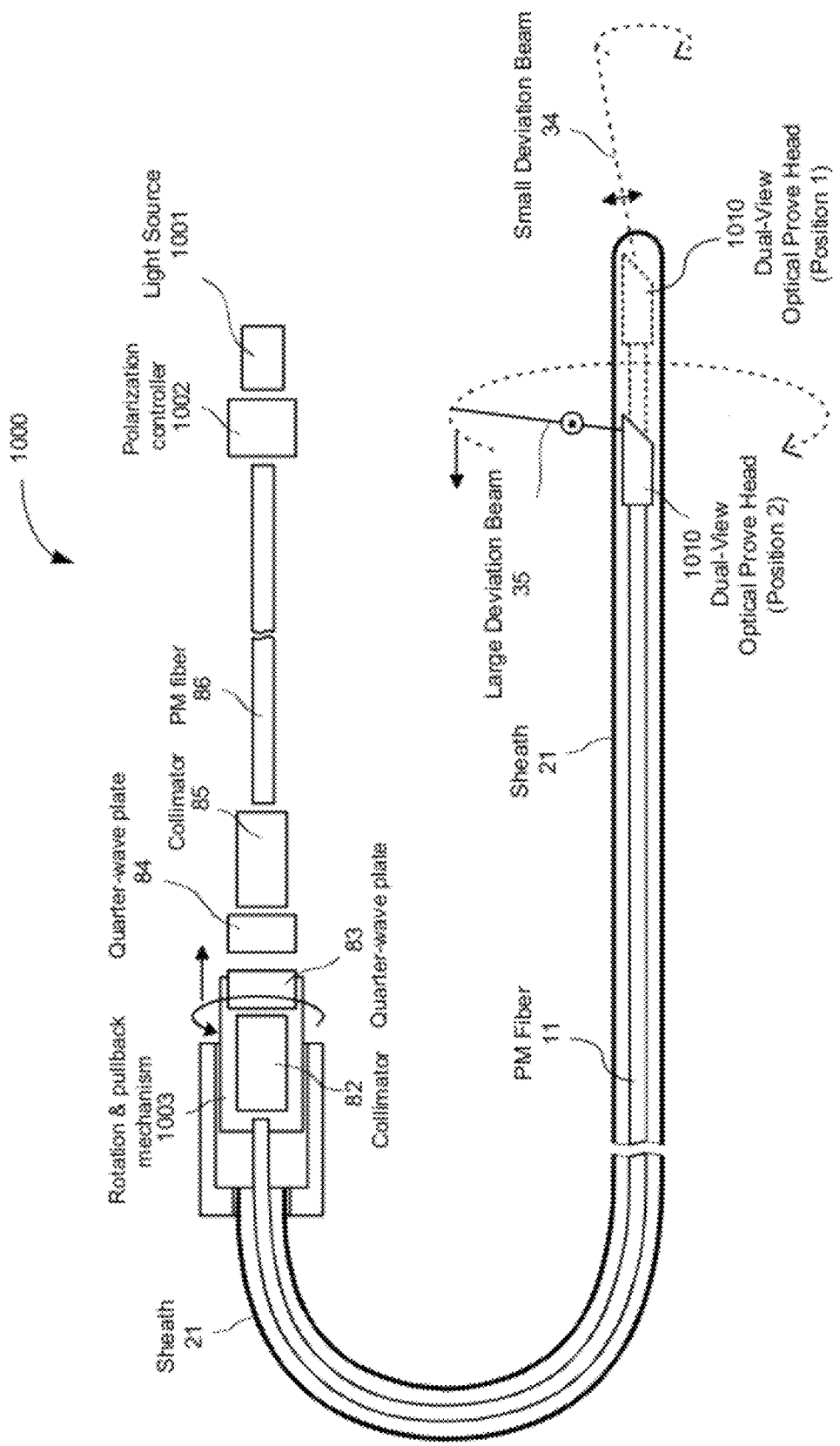
FIG. 10 illustrates one example of an optical probe device that implements the dual-view optical probe head in FIGS. 1A and 1B and the air-spaced fiber optic rotary joint (FORJ) in FIG. 8.

FIG. 10 shows an example of an optical probe system 1000 that implements a variable angle-of-view scanning optical probe head 1010 and a polarization-maintaining FORT in FIG. 8. A rotation and pullback mechanism 1003 is coupled to the rotating assembly of the FORJ to control the position of the probe head 1010 in the sheath 21 by pushing or pulling the PM fiber 11 which may be packaged inside a torque cable and by rotating the PM fiber and the probe head 1010. Two exemplary positions of the probe head 1010 are illustrated to direct the small deviation beam 34 and the large deviation beam 35 to the target, respectively. A light source 1001 is provided to generate a probe beam with a desired spectral range. A polarization controller 1002 is used to control the polarization of the probe beam when entering the PM fiber 86 to direct the probe beam out of the probe head 1010 as either one of the two beams 34 and 35. This system 1000 can be used for, e.g., optical mapping, imaging, analysis of tubular interior of organs and delivery of light-based therapies.

An optical probe head based on the present disclosure can be configured to collect returned light from a target sample that is illuminated by either the large deviation beam 35 or the small deviation beam 34. In one implementation, such an optical probe head, which is coupled to the distal end of the PM fiber 11 to receive the input beam from the PM fiber 11, is structured to reflect a first portion of the input beam back to the PM fiber 11 and direct a second portion of the input beam to the sample. The probe head is also configured to overlap reflection of the second portion from the sample with the first portion and to export to the PM fiber 11 the reflection as a reflected second portion. This feature of generating the first portion of light that does not reach the sample in the optical probe head enables optical detection based on differential delay modulation and processing to extract information from the sample at different penetration depths within the sample. In this regards, a differential delay modulator can be provided to be in optical communication with the proximal end of the PM fiber 11 to receive light in the first portion and the reflected second portion from the proximal end of the PM fiber 11. The differential delay modulator is operable to split the received light into a first beam and a second beam and to produce variable relative phase delays between the first beam and the second beam. A detection module can be provided to detect light that combines the first beam and the second beam and is output by the differential delay modulator. The detection module is operable to extract information of the sample carried by the reflected second portion at different depths in the sample based on the variable relative phase delays produced by the differential delay modulator. These features can be implemented based on disclosures in PCT Publication No. Wo2005/001522 entitled "Measurements of Optical Inhomogeneity and Other Properties in Substances using Propagation Modes of Light" and published on Jan. 6, 2005, and U.S. Pat. No. 6,943,881 entitled "Measurements of Optical Inhomogeneity and Other Properties in Substances Using Propagation Modes of Light," U.S. Pat. No. 6,903,820 entitled "Measurements of Substances Using Two Different Propagation Modes of Light Through a Common Optical Path," and U.S. Pat. No. 7,259,851 entitled "Optical Measurements of Properties in Substances Using Propagation Modes of Light." The entire disclosures of these patent documents are incorporated by reference as part of the specification of this application.

FIGS. 11A and 11B show one example of an optical probe head capable of the dual-view operation as described in FIGS. 1A and 1B and generating the first portion of light that does not reach the sample in the optical probe head for detection based on optical differential delay modulation. This example is based on the dual-view optical probe head design in FIGS. 5A and 5B and other dual-view designs in this application may also be used. An optical partial reflector 1140 is formed between the distal end of the PM fiber 11 and the GRIN lens 53 to partially transmit the probe light to the sample as either the small deviation beam 34 or the large deviation beam 35 and to partially reflect the probe light as the reflection signal 1110 which does not reach the sample. The returned light from the sample is the collected light 1120. The light 1120 and the light 1110 are combined in the PM fiber 11 which directs the combined light to the differential delay modulator for processing. In one implementation, the partial reflector 1140 can be the end facet of the PM fiber 11 which is polished without angling to produce the reflection 1110. Because of the reciprocity, a portion of the light 1120 from the tissue sample is collected by the head and co-propagates with reflection 1110 in the PM fiber 11 back to the proximal location. The reflection 1110 and collected light 1120 from the tissue are processed to form cross-sections of the tissue.

Figure 12:
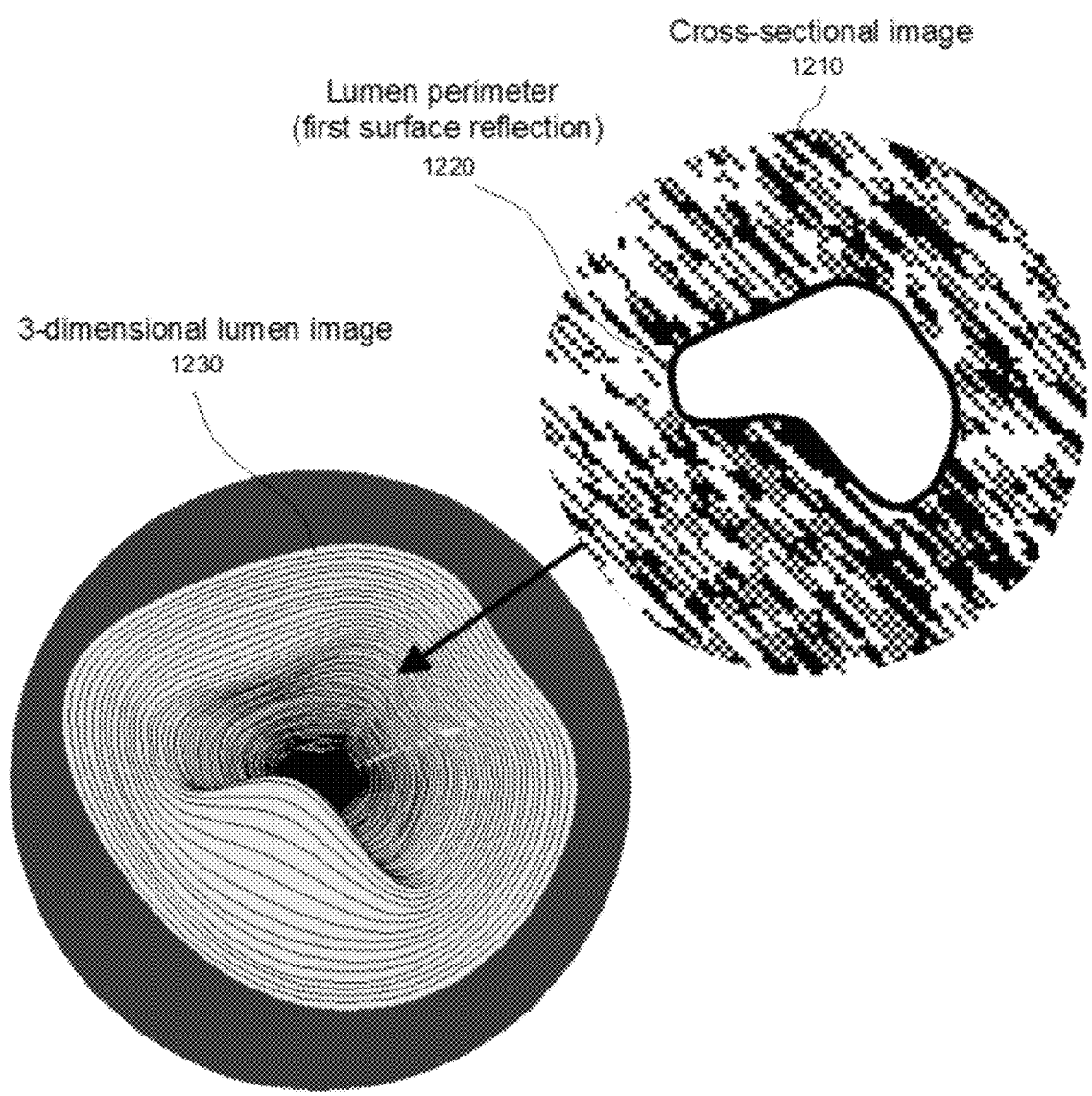
FIG. 12 illustrates one operation of an optical probe head based on the dual-view design in FIGS. 1A and 1B to obtain three-dimensional lumen images of an organ.

The use of the variable angle-of-view scanner in imaging a sample allows for intraluminal mapping that mimics a distal camera, resulting in three-dimensional images of lumenal interiors. FIG. 12 illustrates one example. The process of obtaining the three-dimensional images can be implemented by the following steps: 1) launch one polarization to activate one of the two output beams to interact with the sample; 2) rotate the scanner to acquire an image of the tissue cross-section swept by the beam as illustrated by image 1210; 3) extract the lumenal perimeter 1220 by tracing the first surface reflection from the cross-section; 4) pull the scanner against the sheath to a new longitudinal position; 5) iterate steps 2 through 4 until a desirable range of depths is covered; 5) switch the polarization launched and repeat steps 1 through 4, if needed; and 6) organize all the lumenal perimeters to form the three-dimensional image 1230. It is practical to refresh the cross-sectional images at video rates or higher. Therefore, a highly detailed three-dimensional lumen image (e.g., image 1230) can be constructed in a short processing time depending on the processing algorithm and the computer processing speed, e.g., a few seconds on a PC.

This three-dimensional lumenal imaging technique, namely, virtual camera wire, can be used in conjunction with CT-based navigation systems for navigating vascular or bronchial trees. Performing the CT-based navigation involves acquiring CT scans of the patient, prior to catheterization, to form a digital model of the vascular or bronchial tree. During the catherization, the position of the guidewire/catheter probe tip is determined through communicating electromagnetically with the tip. The computed position is then registered in the roadmap to guide further advances of the guidewire or the catheter. The positioning error of the CT-based navigation systems is typically several millimeters. This error can severely limit the success rate of the procedures. The virtual camera wire technique disclosed in this application can be used to view the lumen interior in both the forward-looking and side-looking directions. As the optical probe can be as small as sub-millimeter in diameter it can be inserted in practically any working channels. The three-dimensional images provided via the virtual camera wire can correct the errors of the CT-based navigation systems, enabling much more accurate, safe and expeditious navigation. Furthermore, the cross-sectional images of the tissues acquired during the process are of additional clinical value, and in some cases, of primary clinical value.

The head design in FIGS. 11A and 11B can be used to generate the first portion of light that does not reach the sample in the optical probe head and to enable optical detection based on differential delay modulation and processing to extract information from the sample at different penetration depths within the sample. This design allows for superposition and interplay of different optical waves and modes propagating along substantially the same optical path provided by the PM fiber 11. When one of the optical waves or modes interacts with the substance under study its superposition with another wave or mode can be used for acquiring information about the optical properties of the substance. This use of a common optical path for different optical waves which may be in the same mode or different modes avoids separation of the reference light beam from the sample light beam in various optical coherence domain reflectometry (OCDR) systems and associated technical issues caused by the separation of optical paths such as uncontrolled fluctuations in the relative optical phase or differential delay between the two beams that may adversely affect the measurements. The use of the common optical path for different optical waves in the same or different modes may be advantageously used to stabilize the relative phase among different radiation waves and modes in the presence of environmental fluctuations in the system such as variations in temperatures, physical movements of the system especially of the waveguides, and vibrations and acoustic impacts to the waveguides and system. In this context, such systems have a "built-in" stability of the differential optical path by virtue of their optical designs and are beneficial for some phase-sensitive measurement, such as the determination of the absolute reflection phase and birefringence.

Figure 13:
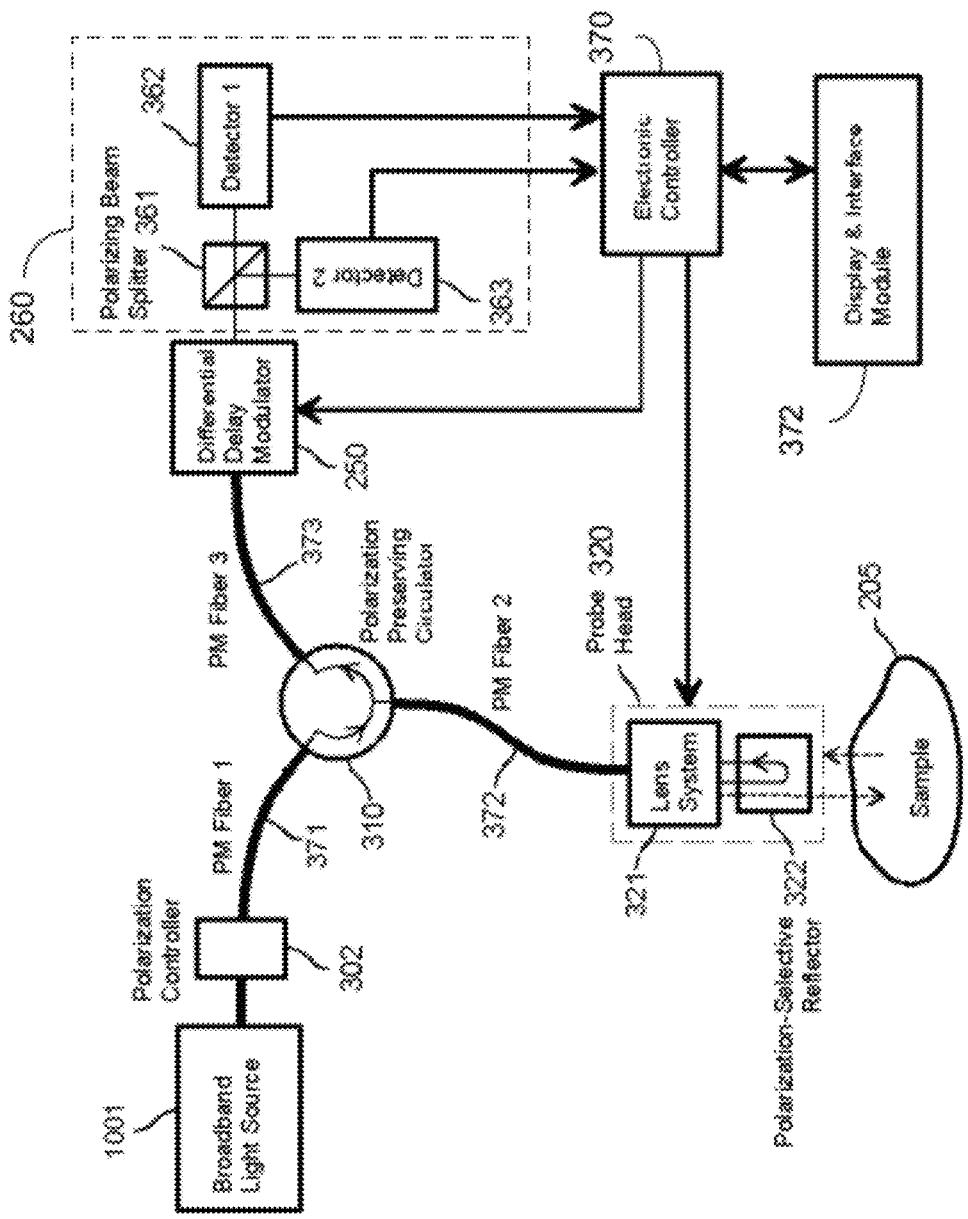
FIG. 13 illustrates an exemplary optical probe system for acquiring images of a target using a dual-view optical probe head design based on the design in FIGS. 11A and 11B.

FIG. 13 shows an exemplary implementation of an optical probe system based on the optical head design in FIGS. 11A and 11B. The spectrum of a light source 1001 may be chosen to satisfy the desired ranging resolution. The broader the spectrum is the better the ranging resolution. Various light sources may be used as the source 1001. For example, some semiconductor superluminescent light emitting diodes (SLED) and amplified spontaneous emission (ASE) sources may possess the appropriate spectral properties for the purpose. In this particular example, a polarization controller 302 may be used to control the state of polarization in order to proportion the magnitudes of two polarization modes 001 and 002 in the input waveguide 371. The waveguide 371 and other waveguides 372 and 373 may be dual-mode waveguides and are capable of supporting two independent polarization modes which are mutually orthogonal. One kind of practical and commercially available waveguide is the polarization maintaining (PM) optical fiber. A polarization maintaining fiber can carry two independent polarization modes, namely, the s-wave polarized along its slow axis and the p-wave polarized along its fast axis. In good quality polarization maintaining fibers these two modes can have virtually no energy exchange, or coupling, for substantial distances. Polarization preserving circulator 310 directs the flow of optical waves according to the following scheme: the two incoming polarization modes from fiber 371 are directed into the fiber 372; the two incoming polarization modes from fiber 372 are directed to the fiber 373. A polarization-preserving circulator 310 may be used to maintain the separation of the two independent polarization modes. For instance, the s-wave in the fiber 371 should be directed to the fiber 372 as s-wave or p-wave only. Certain commercially available polarization-preserving circulators are adequate for the purpose.

The optical probe head 320 is coupled to the waveguide 372 for optically probing the sample 205. The probe head 320 delivers a portion of light received from the waveguide 372, the light in one mode (e.g., 002) of the two modes 001 and 002, to the sample 205 and collects reflected and back-scattered light in the same mode 002 from the sample 205. The returned light in the mode 002 collected from the sample 205 carries information of the sample 205 and is processed to extract the information of the sample 205. The light in the other mode 001 in the waveguide 372 propagating towards the probe head 320 is reflected back by the probe head 320. Both the returned light in the mode 002 and the reflected light in the mode 001 are directed back by the probe head 320 into the waveguide 372 and to the differential delay modulator 250 and the detection system 260 through the circulator 310 and the waveguide 373.

In the illustrated implementation, the probe head 320 includes a lens system 321 and a polarization-selective reflector (PSR) 322. The lens system 321 is to concentrate the light energy into a small area, facilitating spatially resolved studies of the sample in a lateral direction. The polarization-selective reflector 322 reflects the mode 001 back and transmits the mode 002. Hence, the light in the mode 002 transmits through the probe head 320 to impinge on the sample 205. Back reflected or scattered the light from the sample 205 is collected by the lens system 321 to propagate towards the circulator 310 along with the light in the mode 001 reflected by PSR 322 in the waveguide 372.

The detection system 260 in FIG. 13 includes a polarizing beam splitter 361, and two photodetectors 362 and 363. The polarizing beam splitter 361 is used to receive the two independent polarization modes 001 and 002 from the modulator 250 and superposes the two independent polarization modes 001 and 002. The beam splitter 361 may be oriented in such a way that, each independent polarization is split into two parts and, for each independent polarization mode, the two split portions possess the same amplitude. This way, a portion of the mode 001 and a portion of the mode 002 are combined and mixed in each of the two output ports of the beam splitter 361 to form a superposed new mode and each photodetector receives a superposed mode. The polarizing beam splitter 361 may be oriented so that the incident plane of its reflection surface makes a 45-degree angle with one of the two independent polarization mode, 001 or 002.

The system in FIG. 13 further implements an electronic controller or control electronics 370 to receive and process the detector outputs from the photodetectors 362 and 363 and to control operations of the systems. The electronic controller 370, for example, may be used to control the probe head 320 and the differential delay modulator 250. Differential delay modulator 250, under the control of the electronics and programs, generates a form of differential phase modulation as the differential path length scans through a range that matches a range of depth inside the sample 205. The electronic controller 370 may also be programmed to record and extract the amplitude of the oscillation in the measured signal at various differential path lengths generated by the modulator 250. Accordingly, a profile of reflection as a function of the depth can be obtained as a one-dimensional representation of the sample inhomogeneity at a selected location on the sample 205.

In acquiring two-dimensional images of optical inhomogeneity in the sample 205, the probe head 320 may be controlled via a position scanner such as a translation stage or a piezo-electric positioner so that the probing light scans in a lateral direction, perpendicular to the light propagation direction. For every increment of the lateral scan a profile of reflection as a function of depth can be recorded with the method described above. The collected information can then be displayed on a display and interface module 372 to form a cross-sectional image that reveals the inhomogeneity of the sample 205.

In some imaging procedures, a lateral scanning mechanism may be implemented in a device described in this application to change the relative lateral position of the optical probe head and the sample to obtain a 2-dimensional map of the sample. A xy-scanner, for example, may be engaged either to the optical head or to a sample holder that holds the sample to effectuate this scanning in response to a position control signal generated from the electronic controller 370.

FIG. 14 shows one exemplary system for acquiring information of optical inhomogeneity and other properties in substances with only one propagation mode for both the light interacting with the sample and the reflected light that does not reach the sample. A broadband or low-coherence light from Broadband Light Source 1001 is directed to a probe head 2110 in a single optical polarization mode by means of polarization-maintaining waveguides 271 and 272. A partial reflector inside the probe head 2110 reverses the direction of a small portion of the input light to create a radiation wave 1 while transmitting the remainder of the input light to the sample 205. Backscattered or reflected light from the sample 205 becomes a second radiation wave 2 and is collected by the probe head 2110. The probe head 2110 combines and couples both the radiation waves 1 and 2 back into the waveguide 272. The radiation waves 1 and 2 travel in the waveguide 272 towards Light the light director 210 which directs radiation waves 1 and 2 through the waveguide 273 towards the detection module 2101. Notably, the radiation waves 1 and 2 output from the probe head 2110 are in the same optical polarization mode as the input light to the probe head 2110. The probe head 2110 does not change the mode of light when directing the radiation waves 1 and 2 to the waveguide 272.

The detection module 2101 includes a beam Splitter 2120, two optical paths 2121 and 2122, an optical variable delay element 2123 in the path 2122, a beam combiner 2130, and two optical detectors 2141 and 2142. The beam splitter 2120 splits the light in the waveguide 273, which includes the radiation waves 1 and 2 in the same mode, into two parts that respectively propagate in the two optical paths 2121 and 2122. Notably, each of the two parts includes light from both the radiation waves 1 and 2. The variable delay element or delay line 2123 in the optical path 2122 is controlled by a control signal to adjust the relative optical delay between the two optical paths 2121 and 2122 and may be implemented by, e.g., the exemplary delay elements described in this application and other delay designs. The beam combiner 2130 combines the signals of the two optical paths to overlap with each other and to output two optical signals for optical detectors 2141 and 2142, respectively. The beam combiner may be a polarization beam splitter which splits the combined light into two parts, orthogonal in polarization to one another.

The probe head 2110 may include a partial reflector to produce the radiation wave 1 which does not reach the sample 205. One example of the probe head 2110 is shown in FIGS. 11A and 11B. Assuming the single propagation mode for the light to the probe head 2110 and the light out of the probe head 21110 is a polarization mode, the light reflected from the partial reflector in the probe head 2110, i.e., the radiation wave 1, has the same polarization as the light collected from the sample, the radiation wave 2. Therefore, both Radiation 1 and 2 travel in the same propagation mode in the waveguides, 272 and 273. Because the radiation waves 1 and 2 are reflected from different locations, they experience different optical path lengths when reaching the beam splitter 2120. The effect of variable delay element 2123 is to add an adjustable amount of the delay in the light in the path 2122 relative to the light in the path 2121.

In operation, the variable delay element 2123 can be adjusted so that the partial radiation 1 reaching the polarization beam splitter 2130 through the path 2122 can be made to experience a similar optical path length as the partial radiation 2 reaching the beam splitter 2130 via the other path 2121. The superposition of the two beams at the photo detectors 2141 and 2142 causes a measurable intensity variation as their relative path length is being varied by the variable delay element 2123. This variation can be utilized to retrieve information on the inhomogeneity and other properties of the sample 205.

The dual-view optical probe head in FIGS. 1A and 1B may also be used in OCDR systems in medical diagnoses and certain OCDR systems known as optical coherence tomography (OCT) systems. FIG. 15 illustrates an example of an OCDR system having a dual view optical probe head 1500. A beam splitter 1601 is used to split the probe beam from the light source 1001 into a probe beam and a reference beam. The beam splitter 1501 is engaged to two optical fibers 1610 and 1620 that respectively guide the probe and reference beams in a Michelson interferometer configuration. The fiber 1510 forms part of the sample arm whose distal end is engaged to the dual view optical probe head 1500. The probe head 1500 directs the probe beam to the sample in form of either one of the large deviation beam 35 and the small deviation beam 34 as shown in FIGS. 1A and 1B. The returned light from the sample is collected by the probe head 1500 and is directed back to the fiber 1520 back to the beam splitter 1501. The reference beam travels in the reference waveguide arm 1510 to a scanning delay line 1512 which includes a reference reflector to reflect the reference light back to the reference fiber 1510 and the beam splitter 1501. The light from the sample and the reference light mixes with each other at the beam splitter 1501 and optically interferes with each other to produce an optical interference signal. This signal is directed to an optical detector 1530 for detection. The delay of the reference beam in the fiber 1510 can be adjusted by controlling the scanning delay line 1512 to select light from different depths of the sample to interfere with the reference beam. A signal processor 1540 receives the detector output from the detector 1530 and processes the interference signal to obtain the image or other measurement of layers of the sample at different depths.

In view of the above examples, the dual-view optical probe head design illustrated in FIGS. 1A and 1B can be implemented using various optical components in various configurations. In addition, such a dual-view optical probe head can be implemented or incorporated in different optical delivery systems, such as optical delivery systems shown in FIGS. 13 and 14 with a common optical path for two different light beams generated by the optical probe head and the optical delivery system shown in FIG. 15 based on a Michaelson interferometer design with two separated optical paths for the reference beam and the probe beam.

Referring to FIG. 16, in these and other implementations, probe light is directed from a proximal terminal or end of a polarization-maintaining fiber to a distal terminal of the fiber to interact with a target at or near the distal terminal of the fiber (Step 1601) and the optical polarization of the probe light is controlled to direct the probe light at one of two different directions to the target. The probe light at the distal terminal of the fiber is split into a first beam in a first principal polarization of the fiber propagating at a first deviation angle with respect to the fiber and a second beam in a second principal polarization of the fiber propagating at a second deviation angle that is different from the first deviation angle (Step 1602). The polarization of the probe light entering the proximal terminal of the fiber is controlled to be at the first principal polarization of the fiber to maximize optical power, at the distal terminal of the fiber, in the first beam while suppressing optical power in the second beam (Step 1603). Under this polarization condition, the first beam is directed to reach a first region of the target while blocking the second beam from reaching a second region of the target that is different from the first region (Step 1604). If needed, the first beam can be rotated to scan on a cone formed by the first deviation angle to interact different portions of the target in the first region in the optical path of the rotating first beam (Step 1605). Next, the polarization of the probe light entering the proximal terminal of the fiber can be controlled to be at the second principal polarization of the fiber to maximize optical power, at the distal terminal of the fiber, in the second beam while suppressing optical power in the first beam (Step 1606). The second beam is then directed to reach the second region of the target while blocking the first beam from reaching the second region of the target (Step 1607) and can be rotated to scan on a cone formed by the second deviation angle to interact with different portions of the target in the second region in the optical path of the rotating second beam (Step 1608).

An optical probe head can be movably placed inside the hollow channel of a transparent sheath inserted inside the target to deliver the probe light to different locations of the target by sliding the optical probe head inside the sheath. Assuming the first deviation angle is a small deviation angle for obtaining a front view of the first region in front of the distal end of the sheath and the second deviation angle is a large deviation angle for obtaining a view of the second region of the target along the length of the sheath, the optical probe head can then be moved along the sheath at different positions to obtain images of different portions of the target along the length of the sheath. The returned light from the optical probe head can be processed to extract lumenal perimeters at various sliding positions of the optical probe head and the luminal perimeters obtained by suing the second beam and the images obtained from the first beam in the first region can be digitally composed to construct three-dimensional images of the lumen.

In addition, a separate imaging technique may be used simultaneously to capture images of the target and the captured images can be used to guide the distal end of the sheath and the optical probe head inside the sheath to one or more desired locations. For example, a computer tomography (CT) scan imaging system may be used to as a navigation guide for positioning the dual-view optical probe head. The images of the CT scan can be used to introduce a guidewire or catheter with the dual-view optical probe head to a position near a site of interest, for instance, a point of bifurcation. The dual-view optical probe head is then used to perform measurements and the measurements are processed to construct three-dimensional images of the lumen. Based on the constructed three-dimensional images of the lumen, the dual-view optical probe head in the guidewire or the catheter can be adjusted to precisely positioned at the site of interest for additional measurements.

The present dual-view optical probe head designs can be used to provide interactions with tissues and organs in conducting study of tissue physiology and in diagnostic and therapeutic procedures. In many applications of light it is desirable to deliver light to small-size internal organs such as coronary arteries and bronchus. The present dual-view optical prove head designs can be combined with flexible light guides such as optical fibers to deliver light from a proximal location, in vitro, to a distal locations, in vivo, to scan a focused or collimated light beam at the distal location to optically interrogate tissues in different areas of the organ cavities or channels in a non-invasive manner or in a manner with minimized invasion. The small spaces encountered in these procedures limit the size of the scanner to few millimeters or less in their cross-sections which can be difficult for some beam scanners of fixed scan patterns or angle-of-view to operate. The present dual-view optical probe head designs use polarization sensitive optical components and polarization-maintaining light guides to realize beam scanning with at least two viewing angles.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination Only a few examples and implementations are described. One of ordinary skill in the art can readily recognize that variations, modifications and enhancements to the described examples may be made.

What is claimed is:

1. A method for imaging a target, comprising:
    directing probe light from a proximal terminal of a fiber to a distal terminal of the fiber to interact with a target at or near the distal terminal of the fiber;
    controlling optical polarization of the probe light to be at one of two different polarization directions when delivered to the target so that the probe light exits the fiber towards the target along a first beam direction when in a first polarization direction of the two different polarization directions and along a second, different beam direction when in a second polarization direction of the two different polarization directions;
    controlling the optical polarization of the probe light at the target in the two different polarization directions at different times, respectively, to obtain optical image information of the target in a first region of the target when the probe light is controlled to be at the first polarization direction and to obtain optical image information of the target in a second region of the target when the probe light is controlled to be at the second polarization direction;

adjusting a position of the distal terminal of the fiber relative to the target to obtain optical images of the target at different positions along a longitudinal direction of the fiber;

operating a light director to direct the probe light from a light source into the proximal terminal of the fiber which guides the probe light to the distal terminal of the fiber at a target location in the first or second region of the target;

directing a first portion of the probe light at the distal terminal of the fiber to propagate away from the target location towards the proximal terminal o of the fiber without reaching the target location back into the fiber;

directing a second portion of the probe light at the distal terminal of the fiber to exit the fiber to reach the target location;

collecting reflected light from the target location caused by illumination of the second portion to direct the reflected light in the fiber to overlap with the first portion of the probe light and to co-propagate with the first portion of the probe light along the fiber towards proximal terminal of the fiber, wherein the reflected light from the target location carries optical image information of the target location;

using the light director to output light from the proximal terminal of the fiber, which includes the first portion of the probe light and the reflected light from the target location, along a common optical path to reach a detection module; and operating the detection module to process the output light to obtain the optical image information of the target location.

2. The method as in claim 1, comprising:

adjusting a rotation angle of the probe beam around a rotation axis along the fiber to, in combination with adjusting a position of the distal terminal of the fiber at different positions along the fiber, to obtain three dimensional image information of the target.

3. The method as in claim 1, comprising:

selectively blocking light in one of the two polarization directions from reaching a target while directing light in the other of the two polarization directions to interact with the target; and detecting returned light from the target to extract image information of the target.

4. The method as in claim 1, comprising:

operating the detection module to separate the output light into a first light beam and a second light beam;

subsequently varying a differential delay between the first light beam and the second light beam;

subsequent to varying the differential delay, combining the first light beam and the second light beam into combined light; and processing the combined light to extract optical image information based on different differential delays.

5. The method as in claim 1, comprising:

operating a light source to produce source light;

splitting the source light from the light source into the probe light into the fiber for probing the target and a reference light beam along a reference optical arm that is separate from the fiber;

directing the reference light beam in the reference optical arm to a reference reflector to reflect the reference light beam back to the reference optical arm;

controlling a delay in the reflected reference light beam to produce varying values of the delay;

combining the reflected reference light beam from the reference optical arm and returned probe light from the fiber which carries optical image information of the target location to cause optical interference between the reflected reference light beam from the reference optical arm and returned probe light from the fiber to produce an optical interference signal as a function of the varying values of the delay in the reference light beam; and processing the optical interference signal to extract the optical image information at the target location.

6. A method for imaging a target, comprising:

directing probe light from a proximal terminal of a fiber to a distal terminal of the fiber to interact with a target at or near the distal terminal of the fiber;

controlling optical polarization of the probe light to be at one of two different polarization directions when delivered to the target so that the probe light exits the fiber towards the target along a first beam direction when in a first polarization direction of the two different polarization directions and along a second, different beam direction when in a second polarization direction of the two different polarization directions;

controlling the optical polarization of the probe light at the target in the two different polarization directions at different times, respectively, to obtain optical image information of the target in a first region of the target when the probe light is controlled to be at the first polarization direction and to obtain optical image information of the target in a second region of the target when the probe light is controlled to be at the second polarization direction; and adjusting a position of the distal terminal of the fiber relative to the target to obtain optical images of the target at different positions along a longitudinal direction of the fiber operating a light director to direct the probe light from a light source into the proximal terminal of the fiber which guides the probe light to the distal terminal of the fiber at a target location in the first or second region of the target;

directing a first portion of the probe light at the distal terminal of the fiber to propagate away from the target location towards the proximal terminal o of the fiber without reaching the target location back into the fiber;

directing a second portion of the probe light at the distal terminal of the fiber to exit the fiber to reach the target location;

collecting reflected light from the target location caused by illumination of the second portion to direct the reflected light in the fiber to overlap with the first portion of the probe light and to co-propagate with the first portion of the probe light along the fiber towards proximal terminal of the fiber, wherein the reflected light from the target location carries optical image information of the target location;

using the light director to output light from the proximal terminal of the fiber, which includes the first portion of the probe light and the reflected light from the target location, along a common optical path to reach a detection module; and operating the detection module to modulate a differential delay between the first portion of the probe light and the reflected light from the target location to detect combined light of the first portion of the probe light and the reflected light from the target location under the modulated differential delay to obtain the optical image information of the target location.

\* \* \* \* \*